United States Patent
Booth et al.

(10) Patent No.: US 9,965,596 B2
(45) Date of Patent: *May 8, 2018

(54) MEANS AND METHOD FOR IMPROVED GLYCEMIC CONTROL FOR DIABETIC PATIENTS

(71) Applicant: Aseko, Inc., Greenville, SC (US)

(72) Inventors: Robert C. Booth, Columbus, NC (US); Robert E. Fischell, Dayton, MD (US)

(73) Assignee: Aseko, Inc., Greenville, SC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/677,397

(22) Filed: Aug. 15, 2017

(65) Prior Publication Data

US 2017/0344725 A1    Nov. 30, 2017

Related U.S. Application Data

(63) Continuation of application No. 15/403,880, filed on Jan. 11, 2017, now Pat. No. 9,773,096, which is a continuation of application No. 15/283,838, filed on Oct. 3, 2016, now Pat. No. 9,811,638, which is a continuation of application No. 14/861,427, filed on Sep. 22, 2015, now Pat. No. 9,483,619, which is a continuation of application No. 13/617,776, filed on Sep. 14, 2012, now Pat. No. 9,171,343, which is a
(Continued)

(51) Int. Cl.
| | |
|---|---|
| G06Q 50/22 | (2018.01) |
| G06Q 50/24 | (2012.01) |
| A61M 5/172 | (2006.01) |
| G06F 19/00 | (2018.01) |
| A61B 5/11 | (2006.01) |
| A61B 5/00 | (2006.01) |
| A61B 5/145 | (2006.01) |
| G06F 3/0484 | (2013.01) |

(52) U.S. Cl.
CPC ........ *G06F 19/3468* (2013.01); *A61B 5/0022* (2013.01); *A61B 5/1118* (2013.01); *A61B 5/14532* (2013.01); *G06F 19/3431* (2013.01); *G06F 3/04847* (2013.01)

(58) Field of Classification Search
CPC combination set(s) only.
See application file for complete search history.

(56) References Cited

U.S. PATENT DOCUMENTS

| | | | |
|---|---|---|---|
| 4,055,175 A | 10/1977 | Clemens et al. |
| 4,151,845 A | 5/1979 | Clemens |
| 4,206,755 A | 6/1980 | Klein |
| 4,464,170 A | 8/1984 | Clemens et al. |
| 4,850,959 A | 7/1989 | Findl |
| 5,091,190 A | 2/1992 | Kuczynski et al. |
| 5,614,224 A | 3/1997 | Womack |
| 5,998,363 A | 12/1999 | Forse et al. |

(Continued)

FOREIGN PATENT DOCUMENTS

| | | |
|---|---|---|
| EP | 461207 A1 | 12/1991 |
| EP | 483595 A2 | 5/1992 |

(Continued)

*Primary Examiner* — Maroun P Kanaan

(74) *Attorney, Agent, or Firm* — Honigman Miller Schwartz and Cohn LLP

(57) ABSTRACT

A glycemic control system includes a physician processor, remote processor, and a portable telephone having a data input mechanism, a display, and an internal processor for bi-directional communication with the physician's processor and the remote processor. A patient inputs data to the internal processor responsive to input from the physician's processor and then transmits the information to the remote processor where an optimized number of units to be administered is sent back and displayed on the portable telephone.

24 Claims, 12 Drawing Sheets

Related U.S. Application Data continuation-in-part of application No. 13/610,287, filed on Sep. 11, 2012.

(56)  References Cited

U.S. PATENT DOCUMENTS

| | | |
|---|---|---|
| 6,428,825 B2 | 8/2002 | Sharma et al. |
| 6,472,366 B2 | 10/2002 | Kishino et al. |
| 6,572,542 B1 | 6/2003 | Houben et al. |
| 6,605,039 B2 | 8/2003 | Houben et al. |
| 6,615,081 B1 | 9/2003 | Boveja |
| 6,808,703 B2 | 10/2004 | Park et al. |
| 6,890,568 B2 | 5/2005 | Pierce et al. |
| 6,927,246 B2 | 8/2005 | Noronha et al. |
| 7,498,318 B1 | 3/2009 | Stahl et al. |
| 7,704,226 B2 | 4/2010 | Mueller, Jr. et al. |
| 7,824,333 B2 | 11/2010 | Otto et al. |
| 7,837,622 B2 | 11/2010 | Itoh et al. |
| 7,985,848 B2 | 7/2011 | Woo et al. |
| 8,088,731 B2 | 1/2012 | Knudsen et al. |
| 8,117,020 B2 | 2/2012 | Abensour et al. |
| 8,185,412 B1 | 5/2012 | Harpale |
| 8,198,320 B2 | 6/2012 | Liang et al. |
| 8,204,729 B2 | 6/2012 | Sher |
| 8,257,735 B2 | 9/2012 | Lau et al. |
| 8,318,221 B2 | 11/2012 | Miller et al. |
| 8,329,232 B2 | 12/2012 | Cheng et al. |
| 8,333,752 B2 | 12/2012 | Veit et al. |
| 8,370,077 B2 | 2/2013 | Bashan et al. |
| 8,420,125 B2 | 4/2013 | Webster et al. |
| 8,420,621 B2 | 4/2013 | Lai et al. |
| 8,457,901 B2 | 6/2013 | Beshan et al. |
| 8,527,208 B2 | 9/2013 | Prud'homme et al. |
| 8,548,544 B2 | 10/2013 | Kircher, Jr. et al. |
| 8,571,801 B2 | 10/2013 | Anfinsen et al. |
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,992,464 B2 | 3/2015 | Bashan et al. |
| 2001/0002269 A1 | 5/2001 | Zhao |
| 2003/0199445 A1 | 10/2003 | Knudsen et al. |
| 2003/0208110 A1 | 11/2003 | Mault et al. |
| 2003/0208113 A1 | 11/2003 | Mault et al. |
| 2005/0020681 A1 | 1/2005 | Takayama et al. |
| 2005/0054818 A1 | 3/2005 | Brader et al. |
| 2005/0096637 A1 | 5/2005 | Heruth |
| 2005/0176621 A1 | 8/2005 | Brader et al. |
| 2005/0197621 A1 | 9/2005 | Poulsen et al. |
| 2005/0267195 A1 | 12/2005 | Mikoshiba et al. |
| 2006/0040003 A1 | 2/2006 | Needleman et al. |
| 2006/0078593 A1 | 4/2006 | Strozier et al. |
| 2006/0188995 A1 | 8/2006 | Ryan et al. |
| 2007/0036872 A1 | 2/2007 | Tsuboi et al. |
| 2007/0060796 A1 | 3/2007 | Kim |
| 2007/0160678 A1 | 7/2007 | Guimberteau et al. |
| 2007/0249916 A1 | 10/2007 | Pesach et al. |
| 2007/0282186 A1 | 12/2007 | Gilmore |
| 2008/0119421 A1 | 5/2008 | Tuszynski et al. |
| 2008/0139511 A1 | 6/2008 | Friesen |
| 2008/0299079 A1 | 12/2008 | Meezan et al. |
| 2009/0029933 A1 | 1/2009 | Velloso et al. |
| 2009/0099438 A1 | 4/2009 | Flanders |
| 2009/0110752 A1 | 4/2009 | Shang et al. |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0242399 A1 | 10/2009 | Kamath et al. |
| 2009/0312250 A1 | 12/2009 | Ryu et al. |
| 2010/0121170 A1 | 5/2010 | Rule |
| 2010/0286601 A1 | 11/2010 | Yodfat et al. |
| 2011/0021894 A1 | 1/2011 | Mohanty et al. |
| 2011/0071365 A1 | 3/2011 | Lee et al. |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0173308 A1 | 7/2011 | Gutekunst |
| 2011/0178008 A1 | 7/2011 | Arai et al. |
| 2011/0217396 A1 | 9/2011 | Oldani |
| 2011/0229602 A1 | 9/2011 | Aymard et al. |
| 2011/0286984 A1 | 11/2011 | Huang |
| 2011/0305771 A1 | 12/2011 | Sampalis |
| 2012/0003339 A1 | 1/2012 | Minacapelli |
| 2012/0053222 A1 | 3/2012 | Gorrell et al. |
| 2012/0058942 A1 | 3/2012 | Dupre |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0244096 A1 | 9/2012 | Xie et al. |
| 2012/0295985 A1 | 11/2012 | Miller et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0190583 A1 | 7/2013 | Grosman et al. |
| 2013/0217990 A1 | 8/2013 | Saettel et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |
| 2015/0025903 A1 | 1/2015 | Mueller-Wolf |
| 2015/0031053 A1 | 1/2015 | Moerman |
| 2015/0037406 A1 | 2/2015 | Bernabeu Martinez et al. |

FOREIGN PATENT DOCUMENTS

| | | |
|---|---|---|
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |

(56) References Cited

FOREIGN PATENT DOCUMENTS

| | | |
|---|---|---|
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1115389 A1 | 7/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 2139393 A1 | 1/2010 |
| EP | 2300046 A2 | 3/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2418972 A1 | 2/2012 |
| EP | 2448432 A1 | 5/2012 |
| EP | 2448468 A1 | 5/2012 |
| EP | 2482712 A1 | 8/2012 |
| EP | 2535831 A1 | 12/2012 |
| EP | 2552313 A2 | 2/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2640373 A1 | 9/2013 |
| EP | 2641084 A1 | 9/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| WO | WO-1992019260 A1 | 11/1992 |
| WO | WO-1996009823 A1 | 4/1996 |
| WO | WO-1999044496 A1 | 9/1999 |
| WO | WO-2002036139 | 5/2002 |
| WO | WO-2003024468 | 3/2003 |
| WO | WO-2003077895 | 9/2003 |
| WO | WO-2003094927 | 11/2003 |
| WO | WO-2005081119 A2 | 9/2005 |
| WO | WO-2005081170 A2 | 9/2005 |
| WO | WO-2005081171 A2 | 9/2005 |
| WO | WO-2005081173 A1 | 9/2005 |
| WO | WO-2006022619 A2 | 3/2006 |
| WO | WO-2006022629 A1 | 3/2006 |
| WO | WO-2006022633 A1 | 3/2006 |
| WO | WO-2006022634 A1 | 3/2006 |
| WO | WO-2006022636 A1 | 3/2006 |
| WO | WO-2006022638 A1 | 3/2006 |
| WO | WO-2006044556 A2 | 4/2006 |
| WO | WO-2003101177 | 7/2006 |
| WO | WO-2006079124 A2 | 7/2006 |
| WO | WO-2006091918 A2 | 8/2006 |
| WO | WO-2006130901 A1 | 12/2006 |
| WO | WO-2007149533 A2 | 12/2007 |
| WO | WO-2008005761 A2 | 1/2008 |
| WO | WO-2008013324 A1 | 1/2008 |
| WO | WO-2008124478 A1 | 10/2008 |
| WO | WO-2011094352 A1 | 8/2011 |
| WO | WO-2012047800 A1 | 4/2012 |
| WO | WO-2012065556 A1 | 5/2012 |
| WO | WO-2012097064 A1 | 7/2012 |
| WO | WO-2012148252 A2 | 11/2012 |
| WO | WO-2012161670 A2 | 11/2012 |
| WO | WO-2013040712 A1 | 3/2013 |
| WO | WO-2013050309 A1 | 4/2013 |
| WO | WO-2013086372 A1 | 6/2013 |
| WO | WO-2013108262 A1 | 7/2013 |
| WO | WO-2013134548 A2 | 9/2013 |
| WO | WO-2013172833 A1 | 11/2013 |
| WO | WO-2013177565 A1 | 11/2013 |
| WO | WO-2014011488 A2 | 1/2014 |
| WO | WO-2014012084 A1 | 1/2014 |
| WO | WO-2014023834 A2 | 2/2014 |
| WO | WO-2014024201 A1 | 2/2014 |
| WO | WO-2014028607 A1 | 2/2014 |
| WO | WO-2014068007 A1 | 5/2014 |
| WO | WO-2014075135 A1 | 5/2014 |
| WO | WO-2014099829 A1 | 6/2014 |
| WO | WO-2014106263 A2 | 7/2014 |
| WO | WO-2014145049 A2 | 9/2014 |
| WO | WO-2014149535 A1 | 9/2014 |
| WO | WO-2014149781 A1 | 9/2014 |
| WO | WO-2014152704 A1 | 9/2014 |
| WO | WO-2014162549 A1 | 10/2014 |
| WO | WO-2014164226 A2 | 10/2014 |
| WO | WO-2014179171 A1 | 11/2014 |
| WO | WO-2014187812 A1 | 11/2014 |
| WO | WO-2014190231 A1 | 11/2014 |
| WO | WO-2014202024 A1 | 12/2014 |
| WO | WO-2014209630 A2 | 12/2014 |
| WO | WO-2014209634 A1 | 12/2014 |

PRESCRIPTION TO OBTAIN THE GLYTAPP

I, Stephen S. Smith, MD, hereby provides this prescription for my patient (Patient ID# WJ-000-012) for GlyTec, Inc. to provide the GlytApp to better regulate the patient's blood glucose. I also prescribe the following actions to be taken by the patient and/or his smart phone for certain conditions of hyperglycemia or hypoglycemia.

| BLOOD GLUCOSE READING | ACTION BY PATIENT |
|---|---|
| Between 60 and 70 | Drink one glass of sugared liquid |
| | _____ Notify doctor |
| Between 50 and 59.9 | Drink two glasses of sugared liquid |
| | _____ Notify doctor |
| Between 40 and 49.9 | Drink three glasses of sugared liquid |
| | __X__ Notify doctor |
| Between 200 and 300 | Take _____ Units of Type _____ Insulin |
| | _____ Notify Doctor |
| Between 301 and 400 | Take _____ Units of Type _____ Insulin |
| | _____ Notify Doctor |
| Above 400 | Take _____ Units of Type _____ Insulin |
| | __X__ Notify Doctor |

Signed: _____   Date: _____

FIG. 8

MEANS AND METHOD FOR IMPROVED GLYCEMIC CONTROL FOR DIABETIC PATIENTS

CROSS REFERENCE TO RELATED APPLICATIONS

This U.S. patent application is a continuation of, and claims priority under 35 U.S.C. § 120 from, U.S. patent application Ser. No. 15/403,880, filed on Jan. 11, 2017, which is a continuation of U.S. patent application Ser. No. 15/283,838, filed on Oct. 3, 2016, which is a continuation of U.S. patent application Ser. No. 14/861,427, filed on Sep. 22, 2015, which is a continuation of U.S. patent application Ser. No. 13/617,776, filed on Sep. 14, 2012, which is a continuation-in-part of U.S. patent application Ser. No. 13/610,287, filed on Sep. 11, 2012. The disclosures of these prior applications are considered part of the disclosure of this application and are hereby incorporated by reference in their entireties.

TECHNICAL FIELD

This disclosure is in the field of methods and devices to improve blood glucose control for diabetic patients.

BACKGROUND

A background. the last several years, improved control of blood glucose for patients in the hospital using the G+ algorithm created by Aseko, Inc. for patients on intravenous insulin injection has been shown to significantly improve glycemic control. Improved glycemic control is achieved when the patient does not experience hypoglycemia (too low a blood glucose) or hyperglycemia (too high a blood glucose). Blood glucose levels below 70 mg/dl are considered to be a condition of hypoglycemia and fasting blood glucose levels above 140 mg/dl are considered to be a condition of hyperglycemia. The G+ algorithm is used by hospitals to prevent both hypoglycemia and hyperglycemia. This is accomplished in the following way: first, the nurse would measure the patient's blood glucose and place that value and the patient's name at a computer station where the nurse is situated; second other pertinent information about the patient (for example, hemoglobin A1C, height, weight, the number of grams of carbohydrates at a recently eaten meal or a meal about to be eaten, etc.) would be provided from that nurse's station computer; third, the hospital's central computer would calculate the dose of insulin to be delivered to that particular patient to maintain normal blood glucose; and fourth, the nurse would administer that number of units of insulin to that patient. Experience over several years has shown that this method has achieved excellent results in reducing the rates of hypoglycemia and hyperglycemia experienced by patients being treated in a hospital.

More recently, GlyTec, LLC. (a subsidiary of Aseko, Inc.) has created an algorithm for improved glycemic control for those patients on subcutaneously injected insulin. By the use of this algorithm, patients having subcutaneously administered insulin either within the hospital or outside the hospital can improve their glycemic control. It would be highly advantageous for patients away from the hospital to experience the improved glycemic control that has been demonstrated using the G+ algorithm at those hospitals where that system is available.

There have recently been several different apps on smart phones that can provide information for the diabetic patient. For example, an app is now available that provides a listing of the specific numbers of carbohydrates for different foods that can be eaten by the diabetic patient to better judge how many units of insulin that are needed to improve that patient's glycemic control after ingesting that number of grams of carbohydrates. However, there is no app currently available that shows a complete listing of foods from which a diabetic patient could select an abbreviated list of those particular foods that that patient would have in his or her normal diet. Still further, no app exists that has in its memory the number of grams of carbohydrates for those specific foods that that specific patient would select. Still further, there is no remote computer system that can communicate with a patient's smart phone which remote computer would have in its memory the number of grams of carbohydrates for an extensive selection of foods from which a specific patient could select a subset of such foods. Still further there is no app that indicates the quantity of a specific food that the patient has eaten or is about to eat. Still further, there is no app available on any smart phone that could make contact with a remote computer system to indicate other conditions experienced by a diabetic patient that affect that patient's need for insulin. For example, there is no existing app that indicates if the patient is undergoing exercise or the severity of such exercise, no app to indicate having significant emotional distress, no app that states if the patient is having a menstrual period, or is about to go to sleep or has just woken up from sleeping, or having a fever of a specific temperature, or any other condition that could affect a specific patient's need for insulin. There is also no remote computer system that can keep a record of the past experiences of a specific patient as to that patient's need for insulin depending on a significant number of factors such as those described above and for that computer to suggest to that patient, based on past experience, the optimum dose of insulin to be subcutaneously injected when that information is requested by a specific app in that patient's smart phone. There is also no smart phone that has been programmed to have the same capability as a remote computer system to record all past patient inputs so as to inform the patient as to the optimum number of units of insulin to inject based upon that patient's past history. Other apps do exist that can keep record of blood glucose levels and insulin usage and share this information with a patient's health care team, including IBGStar Diabetes Manager, which is used in conjunction with a specific blood glucose meter. However, this app does not calculate for the patient the optimum insulin dosage based on that patient's current body chemistry and personal history of insulin usage under similar circumstance, and does not give the patient freedom to use whichever glucose meter he or she prefers.

SUMMARY

One aspect of the disclosure provides a method of determining an insulin dosage value to be administered to a subject including the steps of: (a) providing a remote processor for receiving and storing a first set of subject blood glucose parameters; (b) establishing a time period selected from the group of pre-meal, post meal, mid-sleep, bedtime, or miscellaneous; (c) determining a meal type selected from the group of breakfast, lunch, dinner, or snack; (d) obtaining a blood glucose reading of the subject at a selected one of the time periods and the meal types; and (e) providing a system processor coupled to the remote processor. The system processor is configured to calculate a blood glucose correction dosage dependent on a second set of subject blood glucose parameters, and to adjust the blood glucose correction dosage when the selected time period and the meal type is pre-meal and breakfast respectively as a function of the first and second sets of the subject blood glucose parameters.

Implementations of the disclosure may include one or more of the following features. In some implementations, the first set of subject blood glucose parameters includes a mid-point of a target blood glucose range, a hypoglycemia threshold value, an insulin sensitivity factor, and previous basal and insulin dosage values administered at previous selected time periods and meal types, and meal plan data for the subject. Additionally, the second set of subject blood glucose parameters may include the blood glucose reading of the subject, a hypoglycemia threshold, a mid-point target range of the subject and a subject insulin sensitivity value. In some examples, calculating the blood glucose correction dosage includes the steps of: (a) determining if the blood glucose reading is greater than the hypoglycemia threshold; (b) determining if the blood glucose reading is greater than the mid-point of the target blood glucose range; and (c) calculating a correction dose as a function of the blood glucose reading, the mid-point of the target blood glucose range and the subject insulin sensitivity value when the blood glucose reading is greater than the hypoglycemia threshold and the mid-point of the mid-point of the target blood glucose range. In some examples, calculating a correction dosage includes applying a formula and transmitting the correction dosage to a subject data display and the remote processor when the time period is selected from the group of post-meal, mid-sleep, bedtime or miscellaneous. Calculating the correction dosage when the time period is pre-meal and the meal type is breakfast is followed by the steps of: (a) calculating a basal dosage; and (b) calculating an adjustment to the blood glucose correction dosage as a function of an adjustment factor, the meal plan data and a previous breakfast insulin dosage value. In some examples, the step of calculating the basal dosage includes the steps of: (a) determining whether a previous mid-sleep subject blood glucose reading is available; and (b) determining whether the previous mid-sleep subject blood glucose reading is less than a previous breakfast blood glucose reading; and (c) calculating the basal dosage as a function of an adjustment factor dependent upon the previous mid-sleep subject blood glucose reading and a previous basal dose when the previous mid-sleep subject blood glucose reading is less than the previous breakfast subject blood glucose reading, and an adjustment factor dependent on the adjustment factor dependent on a previous breakfast subject blood glucose reading and a previous basal dose when the subject blood glucose reading is greater than the previous subject blood glucose reading; and (d) transmitting the basal dosage to the subject data display and the remote processor.

In some implementations, calculating the correction dosage is followed by the step of calculating an insulin dosage value when the time period is pre-med as a function of: (1) an adjustment factor, and a previous selected meal type insulin dosage value when the subject is on a meal plan wherein a predetermined number of carbohydrates is prescribed for each of the meal types; and (2) the adjustment factor, an estimated number of carbohydrates to be ingested at a selected meal type and a calculated carbohydrate to insulin ratio when the subject is not on a meal plan.

In some examples, the step of determining a physical parameter of the subject includes the step of determining if the subject is exercising. When the subject is exercising the method further includes determining whether the blood glucose reading is less than a midpoint of a target blood glucose range of the subject. In some examples, the method further includes instructing the subject to ingest a predetermined amount of carbohydrates for each predetermined time interval of exercise.

Another aspect of the disclosure provides an insulin dosage system for optimizing insulin dosages to be administered to a subject. The insulin dosage system includes a glucometer for reading the subject's blood glucose value at a time period selected from the group of pre-meal, post meal, mid-sleep, bedtime, or miscellaneous, for a meal type selected from the group of breakfast, lunch, dinner, or snack. The insulin dosage system also includes a remote processor for recovering and storing a first set of subject blood glucose parameters, and a system processor having a display coupled to the remote processor. The system processor is configured to calculate a blood glucose correction dosage dependent on a second set of subject blood glucose parameters, and adjust the blood glucose correction dosage when the selected time period, and the meal type are pre-meal and breakfast respectively as a function of the first and second sets of the subject blood glucose parameters. In some examples, the first set of subject blood glucose parameters includes a mid-point of a target blood glucose range, a hypoglycemia threshold value, an insulin sensitivity factor, previous basal and insulin dosage values administered at previous selected time periods and meal types, and meal plan data for the subject. The second set of subject blood glucose parameters may include the blood glucose reading of the subject, a hypoglycemia threshold, a mid-point target range of the subject and a subject insulin sensitivity value. In some examples, the system processor may further be configured to: determine if the blood glucose reading is greater than the hypoglycemia threshold; determine if the blood glucose reading is greater than the mid-point of the target blood glucose range; and calculate a correction dose as a function of the blood glucose reading, the mid-point of the target blood glucose range and the subject insulin sensitivity value when the blood glucose reading is greater than the hypoglycemia threshold and the mid-point of the mid-point of the target blood glucose range. In some examples, the insulin dosage system includes a transmitting mechanism for transmitting the correction dosage to a subject data display and the remote processor when the time period is selected from the group of post-meal, mid-sleep, bedtime or miscellaneous. Where the time period is pre-meal and the meal type is breakfast the system processor may be further configured to calculate a basal dosage, and calculate an adjustment to the blood glucose correction dosage as a function of an adjustment factor, the meal plan data and a previous breakfast insulin dosage value. When calculating the basal dosage, the system processor may be further configured to determine whether a previous mid-sleep subject blood glucose reading is available and determine whether the previous mid-sleep subject blood glucose reading is less than a previous breakfast flood glucose reading. Also when calculating the basal dosage, the system processor may be further configured to calculate the basal dosage as a function of an adjustment factor dependent upon the previous mid-sleep subject blood glucose reading and a previous basal dose when the previous mid-sleep subject blood glucose reading is less than the previous breakfast subject blood glucose reading, and an adjustment factor dependent on the adjustment factor dependent on a previous breakfast subject blood glucose reading and a previous basal dose when the subject blood glucose reading is greater than the previous subject blood glucose reading. Finally, when calculating the basal dosage, the system processor may be further configured to transmit the basal dosage to the subject data display and the remote processor. The system processor may be further configured to calculate an insulin dosage value when the time period is pre-med as a function of an adjustment factor, and a previous selected meal type insulin dosage value when the subject is on a meal plan wherein a predetermined number of carbohydrates is prescribed for each of the meal types, and the adjustment factor, an estimated number of carbohydrates to be ingested at a selected meal type and a calculated carbohydrate to insulin ratio when the subject is not on a meal plan. In some examples, the system processor is further configured to calculate a recommended dosage of carbohydrates if the subject is in the process of exercising has exercised within a predetermined time interval of the blood glucose reading. When the subject is exercising, the system processor is further configured to determine whether the blood glucose reading is less than a midpoint of a target blood glucose range of the subject. In some examples, the system processor is further configured to instruct the subject to ingest a predetermined amount of carbohydrates for each predetermined time interval of exercise.

The present disclosure is a means and also a method to improve glycemic control for the diabetic patient who is out of the hospital and is on insulin that is subcutaneously administered, via insulin pumps or multiple daily injections. This disclosure requires a special app for a typical smart phone (such as the IPHONE® or the DROID® phone) that is designed to communicate data relative to glycemic control from the patient's smart phone to a remote computer system and back to the patient's smart phone. For the purposes of this specification, this app shall be called the "GlytApp." An important advantage of the present disclosure is to improve the glycemic control for the diabetic patient who is not in a hospital and who plans to be using insulin that is given subcutaneously, and who can utilize the GlytApp that has been programmed into his or her smart phone.

The basic concept of the present disclosure is that the patient's physician uses his/her computer and the Internet to first obtain a Patient ID# from the company that provides the GlytApp for a specific Patient ID#. This is accomplished by the physician (or any authorized individual who has the right to write a prescription) using the Internet to contact (for example) GlytApp.com. On the computer screen would then appear: "Please enter the patient's name and a Patient ID# will be provided." When the operator would then place the patient's name, a Patient ID# would appear. For example, for a patient name William E. Jones, his Patient ID#, WJ-000-012 could then appear. This ID# would indicate that this is the twelfth patient enrolled whose initials are WJ who would have this ID #. After the first meeting the doctor when writes the patient's name into his computer, a specific Patient ID# will appear on that computer screen. There is a great advantage in using two initials plus six numbers. This combination provides 676 million unique Patient ID# s. In the very unlikely event that there is a duplication, the computer that is controlling the Patient ID# s would alarm the doctor to use different initials for that patient. Another novel advantage of the combination of the patient's initials with a serial number is that if the person typing in the Patient ID# at some future time has the wrong number for a specific patient of that specific doctor, then the computer would inform the person who is typing that the Patient ID# as written is incorrect. By first obtaining a Patient ID# without providing any medical information about that patient, the patient's privacy is readily protected. When only that Patient ID# is used instead of using the patient's name in future communications over the Internet, that patient's privacy is also maintained.

Once the doctor (or nurse or medical assistant) has obtained the Patient ID# for a patient while that patient is still in the doctor's office, the doctor would write a prescription for that patient over the Internet to the company that is providing the GlytApp. The patient at that time will also be given a paper copy of the doctor's prescription and, at the patient's request, that prescription could also be sent to the patient's smart phone or to his/her computer.

The physician would write into that patient's smart phone a prescription covering many factors designed to prevent and to treat both hyperglycemia and hypoglycemia. The patient's app (the GlytApp) would have that prescription written into it typically by communicating with the doctor's computer through the GlytApp remote computer system which is used by that doctor for writing prescriptions for insulin usage for his diabetic patients. Inputs into the prescription section of the GlytApp will include blood glucose target range, insulin type, and basal dose, and other necessary information. The GlytApp could also allow the patient to select from a long list of foods those specific foods that a specific patient would choose to eat. The remote computer system that can receive communications from that patient's GlytApp would be capable of converting those foods selected for a specific meal by the patient as to the number of grams of carbohydrates in that quantity of the foods selected for that specific meal. The GlytApp would select (for example) whether the meal involved either a small, medium or large portion of a specific food. As with food items that come in pieces, such as slices of bread, the GlytApp could also send to a remote computer system the number of such pieces of such food. The remote computer system would be able to calculate for that patient the number of grams of carbohydrates depending on the type and quantity of food ingested or to be eaten in the near future by the patient. It is also conceived that the smart phone itself could add up all the grams of carbohydrates for the type of food and portion size selected by the patient and send the total number of grams of carbohydrates to the remote computer system. If the patient injects a certain number of units of insulin based upon a meal he/she is about to eat, and if the patient then dose not eat that meal, then the GlytApp will provide the information that the patient needs relative to ingesting sugar pills (or equivalent source of glucose) to prevent hypoglycemia.

The algorithm used by the remote computer system to determine the number of units of insulin that the patient should inject will be based upon several factors that include: the type and quantity of food ingested by the patient, the time since that last food ingestion, if a meal is about to be eaten, if the patient is about to exercise, etc. One of the most important capabilities of the remote computer system will be to know past history for each patient and to select a recommended number of units of insulin to be delivered based upon that patient's past history. This very important information is all contained for a specific patient in the memory of the remote computer system. For example, if under somewhat similar conditions, the computer's recommendation led to too high a level of blood glucose, then a subsequent computer recommendation would suggest a somewhat higher level of insulin units to be injected in order to have a more normal blood glucose level. Conversely, if a prior recommendation of units of insulin led to too low a level of blood glucose, then in subsequent recommendations by the remote computer system, a lower number of units of insulin to be injected would be suggested for those same conditions. The remote computer system would also be programmed to adjust for many other factors that affect the patient's blood glucose level such as exercise, having a menstrual period, about to go to sleep, having just awakened from sleep, undergoing emotional distress, sexual activity, or any other factor that the remote computer system will determine over a period of time that affects that specific patient's need for insulin. This key ability to provide the patient with essential health information by way of an accurate calculation of insulin dosage sets this proposed GlytApp apart from the other apps for diabetics as described in the prior art.

For security purposes, for the remote computer system to send an instruction to the patient's smart phone with an insulin recommendation it would be required that the computer know the serial number for that GlytApp of that smart phone. When sending the notice of the number of units of insulin to be injected by the patient, the computer would send to the smart phone some information that makes it known to the patient that the remote computer system knows that it is communicating with that specific patient. For example, the remote computer system might send the message which includes the patient's name or a specific password when it sends to the patient the number of units of insulin to be injected.

One implementation of the present disclosure starts with a physician who will be able to write on his computer a prescription for a specific patient who must have a smart phone in order to utilize the means and method of this disclosure. To keep this prescription confidential, it would be delivered into the patient's smart phone at the doctor's office. Alternatively, the physician could send a new or revised prescription by means of a secure link that identifies the patient by that patient's unique serial number. The physician's prescription would include the type of insulin to be used by the patient, the right to receive instructions from the remote computer system to inform the patient as to the amount of insulin to deliver depending upon several factors including (but not limited to) the number grams of carbohydrates ingested, how long in time since the last meal, how many minutes until the next meal, the number of grams of carbohydrates expected to be ingested at the next meal, whether the patient is about to go to sleep, whether the patient has just awakened from having been asleep, whether the patient is having a menstrual period, the extent as to intensity and time duration relative to the patient undergoing exercise, whether the patient has a fever and stipulating the level of that fever, the extent of sexual activity, what the patient should do in the event of different levels of hypoglycemia or hyperglycemia as experienced by the patient from time to time, etc. The remote computer system that communicates with the patient's smart phone would keep a record of all factors that affect a specific patient's blood glucose and would learn from past experience how to suggest the appropriate number of units of insulin for a specific patient based upon the past experience of that specific patient.

An additional important aspect of the present disclosure is that the patient's physician would also write a prescription into that patient's smart phone as to what that patient should do in the event of hypoglycemia or hyperglycemia. For example, the doctor's prescription could include the recommendation to intake glucose according to certain factors as calculated by the amount of ingested glucose necessary to correct hypoglycemia. This oral glucose to be ingested can be in the form of glucose gel, glucose tablets, orange juice, or other forms. Another prescription from the doctor could suggest that, for any level of hypoglycemia, take the suggested number of sugar pills and then measure the blood glucose 15 minutes later to make sure that the hypoglycemia was not becoming more severe. Also, for more extreme levels of hypoglycemia or hyperglycemia, the doctor's prescription may also automatically call the physician and a designated patient monitor to discuss the situation with that patient.

If high levels of hyperglycemia persist, then the patient's monitor at the company that has provided the GlytApp and/or the patient's doctor would be informed of this condition. The doctor's prescription written into his computer and then transferred to the patient's smart phone could include certain recommendations relative to hyperglycemia such as inject additional units of insulin if the blood glucose reading is too high, measure the blood glucose 15 to 30 minutes later and inject additional insulin if the blood glucose level does not go into a normal range, or cut back on foods with a high level of carbohydrates, or increase exercise, or any other recommendation that would decrease the patient's blood glucose.

The prior art in this area includes only apps capable of recording information the patient inputs, and in some cases providing an uncomplicated method for sharing this information with the patient's doctor. The GlytApp not only incorporates those features, but, importantly, provides a two-way flow of information using an interactive interface whereby the information the patient provides is recorded, processed using a key algorithm, and informs the patient of the optimum dosage of insulin based on a variety of conditions. Because the appropriate insulin dosage for a particular patient at a particular time is dependent upon many factors, many diabetic patients struggle with choosing the exact right dosage for any given set of circumstances. This smartphone app is the only smartphone program that will help patients accomplish improved glycemic control.

Thus an advantage of one of the aspects of the disclosure is to improve a diabetic patient's glycemic control by the use of a special app (the GlytApp) on a patient's smart phone that has two-way communication with a remote computer system that has stored in its memory the past history of that patient's need for insulin based upon a multiplicity of factors that affect that patient's blood glucose level.

Another advantage of the disclosure includes having a means to assure the patient that the communication to that patient's smart phone from the remote computer system is in fact unique for that specific patient.

Still another advantage of the disclosure is to have the patient's smart phone receive a specific doctor directed recommendation as to what that patient should do in the event of experiencing either hyperglycemia or hypoglycemia.

Still another advantage of the disclosure is for the patient's smart phone to notify either or both that patient's physician and/or a patient monitor if that patient experiences a potentially dangerous level of hypoglycemia or hyperglycemia that has been programmed by that patient's doctor for that particular patient.

Still another advantage of the disclosure is for the patient's smart phone to request another blood glucose reading to be taken within a short period of time after a prior reading if that first measured level of blood glucose is potentially dangerous for that patient.

Still another advantage of the disclosure is for either the remote computer system or the patient's smart phone to provide for the patient the range of units of insulin that have been suggested in the past by the remote computer system for similar circumstances so that the patient can be sure that the present suggestion for the number of units of insulin to be injected is within a reasonable range.

Still another important advantage of the disclosure is the unique method that the physician or the physician's assistant would use to have the patient gain access to the GlytApp for that patient's smart phone and having a unique serial number for that patient while maintaining the complete privacy of all medical matters pertaining to that patient.

Still another advantage of the disclosure is that the smart phone itself could be used without a remote computer system to calculate the correct dose of insulin for a patient depending upon historical data of matters that affect the patient's blood glucose that have been stored in the memory of that smart phone.

Still another advantage of the disclosure is that, if the patient fails check in at a specified time interval with his physician, an alert would be sent to that patient indicating the potential need for medical care for that patient.

Another aspect of the disclosure provides a system for improved glycemic control for a diabetic patient. The system includes a smart phone controlled by the diabetic patient that includes a specialized app called a "GlytApp," the smart phone having the capability to be programmed by a medical professional who is authorized to write a prescription into that patient's smart phone that enables that patient to access a remote computer system by means of the GlytApp, the GlytApp being designed to send to the remote computer system that patient's reading of blood glucose as well as several other factors that affect that patient's need for insulin including at least the type and quantity of food that the patient has ingested and also the time when that food was ingested or the time in the future when that food will be ingested. The remote computer system has the capability to calculate an optimized number of units of insulin to be injected by the patient at that time for best controlling that patient's level of blood glucose. The number of units of insulin to be injected is based upon the input parameters provided by the patient's smart phone and also based upon the patient's past history as stored in the memory of the remote computer system, as to the patient's past response to input parameters that affect that patient's need for insulin.

In some examples, the smart phone is also capable of displaying a message from the remote computer system that assures the patient that the number of units suggested for subcutaneous injection by the patient is specifically directed for that specific patient by displaying that patient's name or displaying a password that is known to the patient. In some examples, the smart phone displays a range of the units of insulin previously displayed by the smart phone under similar circumstances that determined in the past the patient's need for injected insulin under similar circumstances.

The patient's smart phone may have the capability to transmit to the remote computer system several additional parameters that affect that patient's need for insulin. These parameters include, but are not limited to, the any one of, several or all of the following parameters: if the patient has been exercising, the severity of any such exercising, if the patient is undergoing significant stress, if the patient is undergoing a menstrual period, if the patient is about to go to sleep, or if the patient is just arising from sleep, or if the patient has a fever and the level of that fever.

The patient's smart phone may display an extensive list of foods and the patient can place onto his or her smart phone a subset of the total list of displayed foods which that patient would normally eat and the smart phone also having a listing as to various quantities of such a subset of foods and the smart phone having the capability to transmit to the remote computer system the type of food eaten by the patient and the relative quantity of that food so that the remote computer system can estimate the quantity of carbohydrates in the food eaten by the patient and thereby provide a message to the patient's smart phone as to the number of units of insulin to be injected to best maintain a normal level of blood glucose at that time for that patient. The quantity of food displayed on the patient's smart phone may be specified in three different levels, namely small, medium, or large. Additionally or alternatively, the quantity of food displayed on the smart phone may be listed as to the number of such food items. Such food items include the number of slices of bread, the number of ears of corn, the number of drinks of an alcoholic beverage, the number of glasses of beer or any similar quantization of items of food eaten by the patient.

In some examples, the smart phone has the capability of displaying, to the patient, what action to take if the patient's blood glucose shows either hypoglycemia or hyperglycemia. In some examples, the action to be taken is programmed into the patient's smart phone by that patient's physician. Additionally or alternatively, the action recommended by the smart phone depends on a specific reading of hyperglycemia or hypoglycemia and/or the state of the patient being either mid-sleep or fasting blood glucose. In some examples, the occurrence of hypoglycemia causes the smart phone to suggest to the patient, that the patient takes pills or food that can increase the level of blood glucose for that patient at that time. The number of pills or the amount of food suggested to the patient being greater when there is a more extreme level of hypoglycemia.

In some implementations, the occurrence of hyperglycemia causes the smart phone to suggest to the patient to take an additional injection of a specific number of units of insulin depending on the level of hyperglycemia.

The occurrence of hyperglycemia may cause the patient's smart phone to recommend taking an additional injection of insulin and measuring that patient's blood glucose again in a period of time between 10 and 60 minutes after receiving that additional injection of insulin. In some examples, the smart phone contacts either or both the patient's physician or a patient monitor to inform that person as to a severe extent of either hypoglycemia or hyperglycemia that is being experienced by the patient.

Yet another aspect of the disclosure provides a method to maintain the confidentiality of medical information for a patient who is receiving the GlytApp app.

The method includes the following steps: (a) having a doctor decide that he wishes to give his patient a prescription to obtain the app (the GlytApp) for that patient's smart phone for optimum glycemic control; (b) having the doctor tell the patient that he would like to prescribe the GlytApp if the patient has a smart phone and is willing to pay a monthly fee to improve his/her glycemic control and the patient agrees to that arrangement; (c) having the doctor then request a serial number for his patient from the company that operates the remote computer system that can communicate with that patient by means of the GlytApp; (d) providing the patient's name to the company by the doctor followed by the doctor receiving over the Internet an appropriate serial number that appears on the doctor's computer; and (e) having the doctor then use that patient's serial number in all communications with the company in order to maintain the confidentiality of all medical information pertaining to that patient.

Another aspect of the disclosure provides a system for improved glycemic control for a diabetic patient. The system comprises a physician processor, a remote processor, and a portable telephone. The remote processor is in data communication and displaced from the physician's processor for calculating an optimized number of units of insulin to be administered at a specific time to the patient. The portable telephone having a data input mechanism and a display. The portable telephone has an internal processor for bi-directional communication with the physician's processor and the remote processor. The internal processor is configured to: (a) receive prescribed data from the physician's processor; (b) receive patient input data taken at least from the group of a glucometer reading at the specific time, type of food to be ingested, type of food previously ingested; (c) transmit the patient input data to the remote processor; and (d) receive from the remote processor the optimized number of units to be administered. The remote processor is configured to: (e) calculate as blood glucose correction dosage dependent upon the patient input data to calculate the optimized number of units to be administered; and (f) transmit the optimized number of units to be administered to the physician's processor and the internal processor. The remote processor and the internal processor may be further configured to transmit and receive a unique set of patient specific identifying data for display on the portable telephone display. In some examples, the internal processor is further configured to display a plurality of previously administered patient specific insulin units based upon previously calculated correction dosages calculated by the remote processor. In some examples, the patient input data includes patient physical condition data, the patient physical condition data taken from at least the group of whether or not the patient is exercising, the severity of the exercise, whether the patient is undergoing stress at the specific time, whether the patient is undergoing a menstrual period, whether the patient has a fever and the patient's temperature.

In some examples, the internal processor is further configured to: (a) display a plurality of foods on the portable telephone display; (b) display a set of quantity amount of each of the foods previously ingested or to be ingested by the patient; and (c) transmit to the remote processor the selected quantity amount and the selected foods which the patient has selected at the specific time. The remote processor may be further configured to calculate the number of carbohydrates associated with the foods and the quantity amounts selected by the patient. The remote processor is further configured to calculate the optimized number of units to be administered based upon the select foods and the quantity amounts selected by the patient. The quantity amount displayed on the portable telephone display is specified as small, medium, or large. In some examples, the prescribed data includes a specific action to be taken dependent on whether the patient's blood glucose level determines whether the patient has hypoglycemia or hyperglycemia.

These and other advantages of the disclosure will become obvious to a person of ordinary skill in this art upon reading the detailed description of this disclosure including the associated drawings as presented herein.

DESCRIPTION OF DRAWINGS

FIG. 8 illustrates the prescription form that would be sent by the patient's physician to the company that would then provide the GlytApp for that patient.

Like reference symbols in the various drawings indicate like elements.

DETAILED DESCRIPTION

Figure 1:
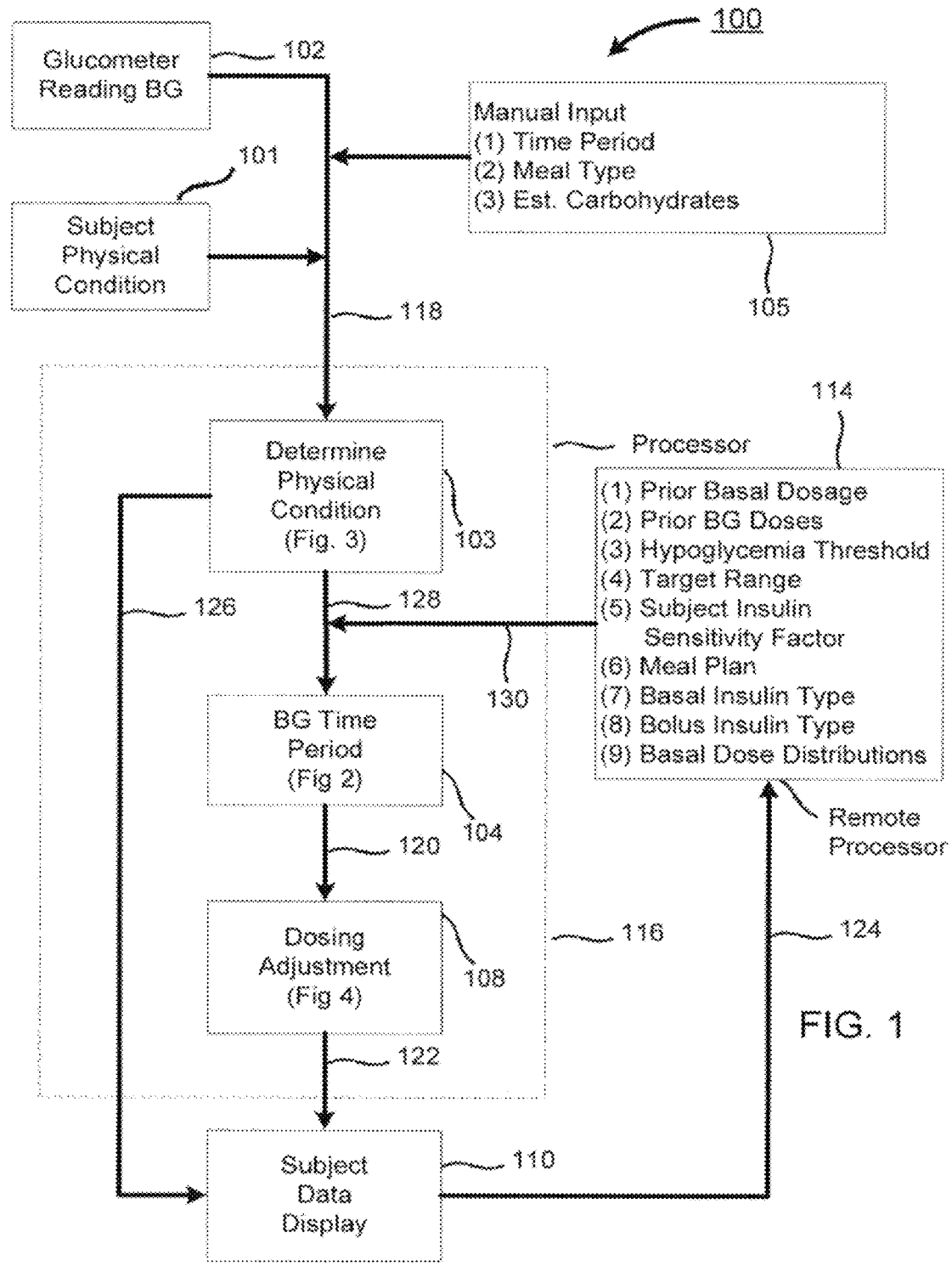
FIG. 1 is a broad flow block diagram of the computer system for processing and calculating insulin dosages to be administered to a subject responsive to a particular meal type and a predetermined time period.

Referring now to FIG. 1, there is shown blood glucose in insulin dosage administering system 100 for determining an insulin dosage value to be administered to a subject. In particular, system 100 is directed to calculating, processing and recommending blood glucose levels for diabetic subjects at specific times prior to or subsequent to ingestion of food or other nutrients and calculating a recommended insulin dose to be administered. System 100 is designed to provide the subject with calculated insulin dosage instructions based upon nutritional and physical information in combination with the personal history of previous insulin administration and resulting blood glucose levels.

The following definitions of the terminology used in the following paragraphs are as follows:

Mid-point target blood glucose range ($T_m$) shall refer to the mid-point of a target blood glucose range (or other blood glucose value within the range) inserted into remote processor 114 by a physician or caregiver for a subject. Although referring to "mid-point" of the blood glucose range, the mid-point target data may be inserted as a function of the mid-point of the mid-point target blood glucose range or some other input deemed appropriate by the subject's physician or caregiver.

Time periods shall refer to the time that a subject is taking a blood glucose reading with a standard glucometer and further refers to a pre-meal time period, a post-meal time period, a bedtime period, a mid-sleep time period, or some miscellaneous time period when the subject is taking the blood glucose reading.

Meal type shall refer to either breakfast, lunch, dinner, snack, or miscellaneous associated with when the subject is taking the subject's blood glucose reading.

Blood glucose reading shall be the blood glucose reading taken at a predetermined time period and associated with a meal type.

Bolus shall refer to recommended insulin dose administered for a meal type and a time period.

Basal Dose shall refer to a total basal dosage of insulin to be taken for one day.

Hypoglycemia threshold shall refer to a lower blood glucose value for a particular subject provided by a physician or other caregiver.

Prior blood glucose doses and/or levels shall refer to previous blood glucose doses and/or levels taken or calculated at previous time periods associated with a respective meal type.

Basal insulin type shall refer to the type or brand of long acting insulin used with basal dose calculations.

Bolus insulin type shall refer to the type or brand of short acting insulin used with meal bolus and correction doses of insulin.

Basal dose distribution shall refer to the frequency and distribution of basal doses for a particular day such as (1) once a day (SID); (2) twice a day (BID); or, (3) three times a day (TID).

Physical condition parameter shall refer to a physical condition of the subject at the time that the blood glucose reading is being taken such as whether or not the subject is exercising or plans to exercise.

Intermediate blood glucose correction dosage shall refer to a first calculation by processor 116 shown in FIG. 1.

Carbohydrate to insulin ratio is a subject specific factor based upon a function of the total daily dose of insulin based upon the subject's weight at the time of initialization of the system 100 processes.

Meal plan shall refer to whether or not the subject is limited to ingesting a known number of carbohydrates for each meal type. When a subject is "on" a meal plan, the subject is generally prescribed a predetermined number of carbohydrates to be ingested at a selected meal type.

Miscellaneous time period shall refer to blood glucose calculations at a time period which is not associated with the time periods of breakfast, lunch, dinner, or snack. Such a miscellaneous time period may be associated with a subject fasting period when blood glucose calculations are being processed.

Mid-sleep time period shall refer to blood glucose readings taken at a time during a time period when the subject is normally asleep, generally at some point during a sleeping cycle of the subject.

Insulin sensitivity factor shall refer to a subject specific sensitivity to insulin, generally determined by a physician or care giver and inserted as a portion of the data stored in the remote processor.

System processor shall refer to an on-site processor which calculates a user's recommended insulin dosage value to be taken at a selected time period and a selected meal type.

Remote processor shall refer to a processor which is coupled to the system processor and stores a first set of a subject's blood glucose parameters and includes but is not limited to prior basal and bolus dosages, prior or previous blood glucose readings for selected meal types and time periods, subject specific hypoglycemia thresholds, prescribed mid-point of a subject's target range, a subject specific insulin sensitivity factor, basal insulin type, bolus insulin type, basal dose distributions, and the number of carbohydrates a subject is recommended to ingest for a selected meal type. The remote processor is generally locationally removed (but in communication) with the system processor, however in some cases the remote processor may be incorporated with the system processor.

Referring now to FIG. 1, there is shown blood glucose system 100 for calculating, processing, determining, and displaying a recommended insulin dosage value (bolus) to be administered to a subject. The broad block diagram shown in FIG. 1 includes a glucometer reading (BG) which is inserted by the subject in block 102. The subject takes his/her blood glucose value with a standard glucometer well-known in the art and commercially available. The glucometer generally provides the subject's current blood glucose reading in mg/dl.

Further, data is inserted by the subject in block 101 as to the physical condition of the subject at the time of the taking of the blood glucose value. The data inserted in block 101 will further be described throughout the flow process and in particular with regard to FIG. 3. In general, data inserted into block 101 includes whether the subject is currently exercising or plans to exercise. Further, data is stored in remote processor 114 associated with prior basal dosages, prior blood glucose doses administered for particular meal types and time periods (bolus), a subject specific hypoglycemia threshold determined by the physician. Data to be included in block 105 is the estimated number of carbohydrates the subject will be ingesting at a particular meal type if the subject is not on a meal plan, as well as the number of carbohydrates recommended to be ingested for a particular meal type if the subject is on a prescribed meal plan. Further included in the data stored in remote processor 114 is the mid-point target blood glucose range and the mid-point ($T_m$) inserted by a physician or other caregiver for a particular subject.

The blood glucose reading taken in block 102 and the subject physical condition in block 101 is inserted into processor 116 on line 118. Within block 103, a determination of the physical condition of the subject is made independent of further calculations within processor 116 to be further detailed in relation to FIG. 3. Block 103 directs processor 116 to decision block 302 in FIG. 3 where the subject indicates whether his condition is exercise. If the condition in decision block 302 is that the subject is not exercising and does not plan to exercise, the information flows on information line 320 back to block 104 in FIG. 1 for further calculations to be further described in following paragraphs. From block 104, the information then flows to dosing adjustment 108 detailed in FIG. 4 and then to subject display 110 and to remote processor 114 for storing the data.

Figure 3:
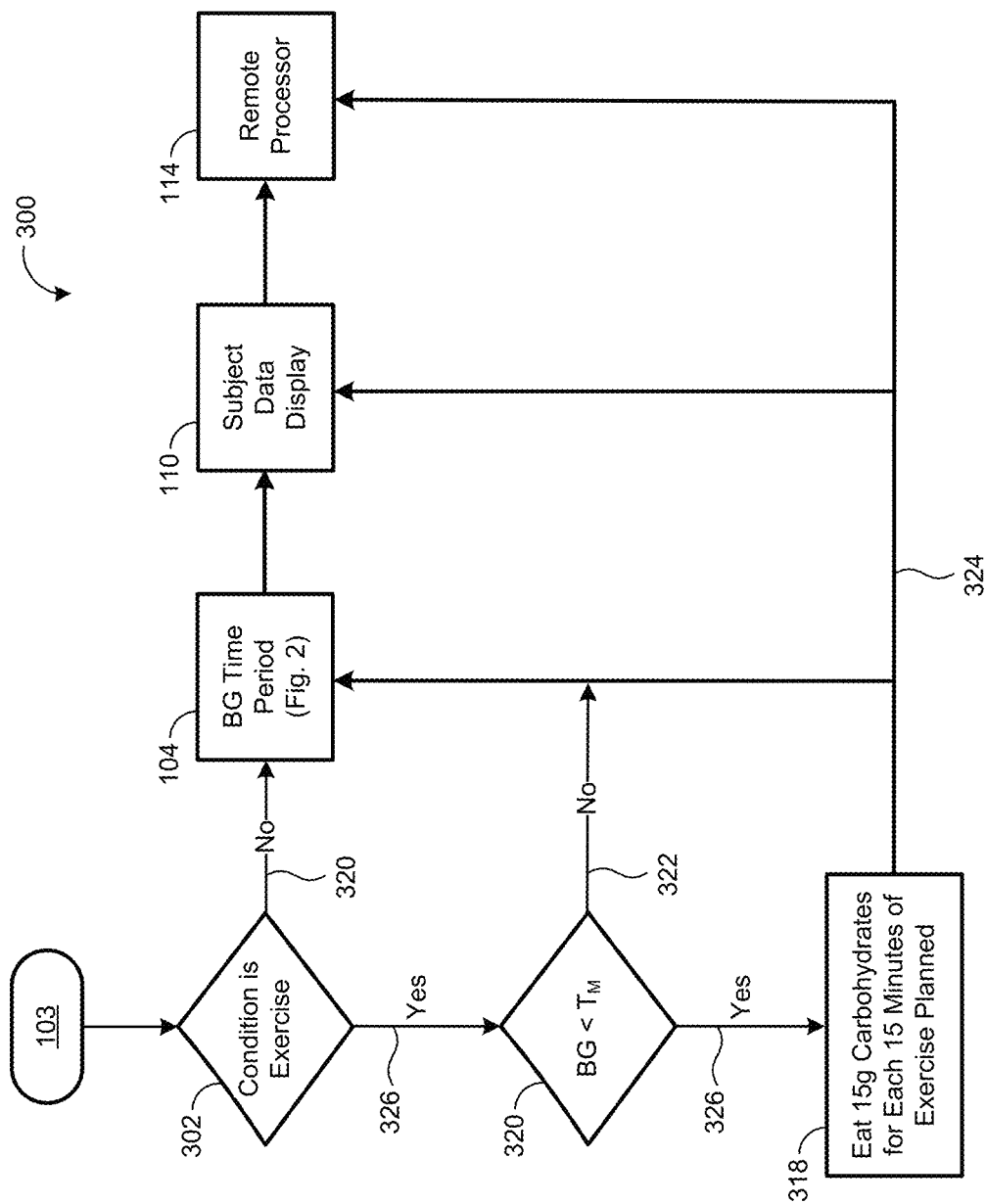
FIG. 3 is an information flow block diagram associated with processing a physical condition of the subject.

If the condition is an exercise condition, found in decision block 302 of FIG. 3, the logic moves on line 326 to decision block 320 where it is determined whether the blood glucose level read in block 102 from the glucometer reading is less than or equal to the mid-point target blood glucose range stored in remote processor 114. If the blood glucose level is equal to or greater than the mid-point target blood glucose range, information is directed on line 322 to block 104 in FIG. 1 for further calculations and passes subsequently to display 110 and remote processor 114.

If the blood glucose level value in decision block 320 is found to be less than the mid-point target blood glucose range, information is directed on line 326 to block 318 where the subject is instructed to eat a predetermined amount of carbohydrates for each predetermined minutes of exercise being planned or having been accomplished. This instruction is then provided to the patient on subject display 110 on line 324 and the information is additionally sent to remote processor 114 for storage of the instructions.

Figure 2:
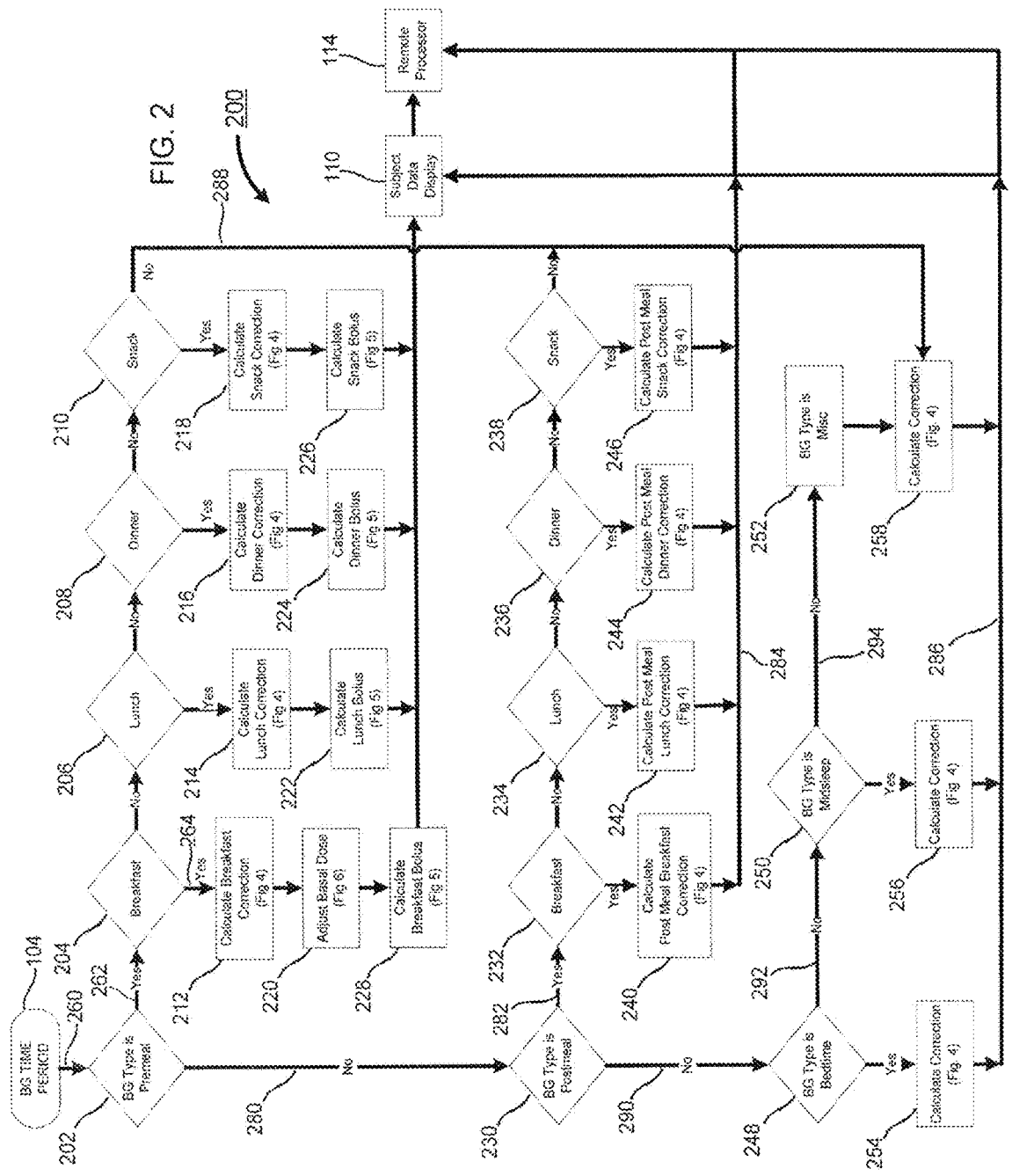
FIG. 2 is a logic block diagram providing a broad logic flow of the logic associated with the computer system and modules dependent upon whether the meal type is pre-meal, post-meal, bedtime, mid-sleep, or miscellaneous.

Thus, whether the condition is exercise determined in decision block 302, or whether or not the blood glucose level is less than the mid-point of the target blood glucose range determined in decision block 320, all logic then passes to blood glucose time period block 104 shown in FIG. 1 where the processing of block 104 is initiated in FIG. 2.

Figure 4:
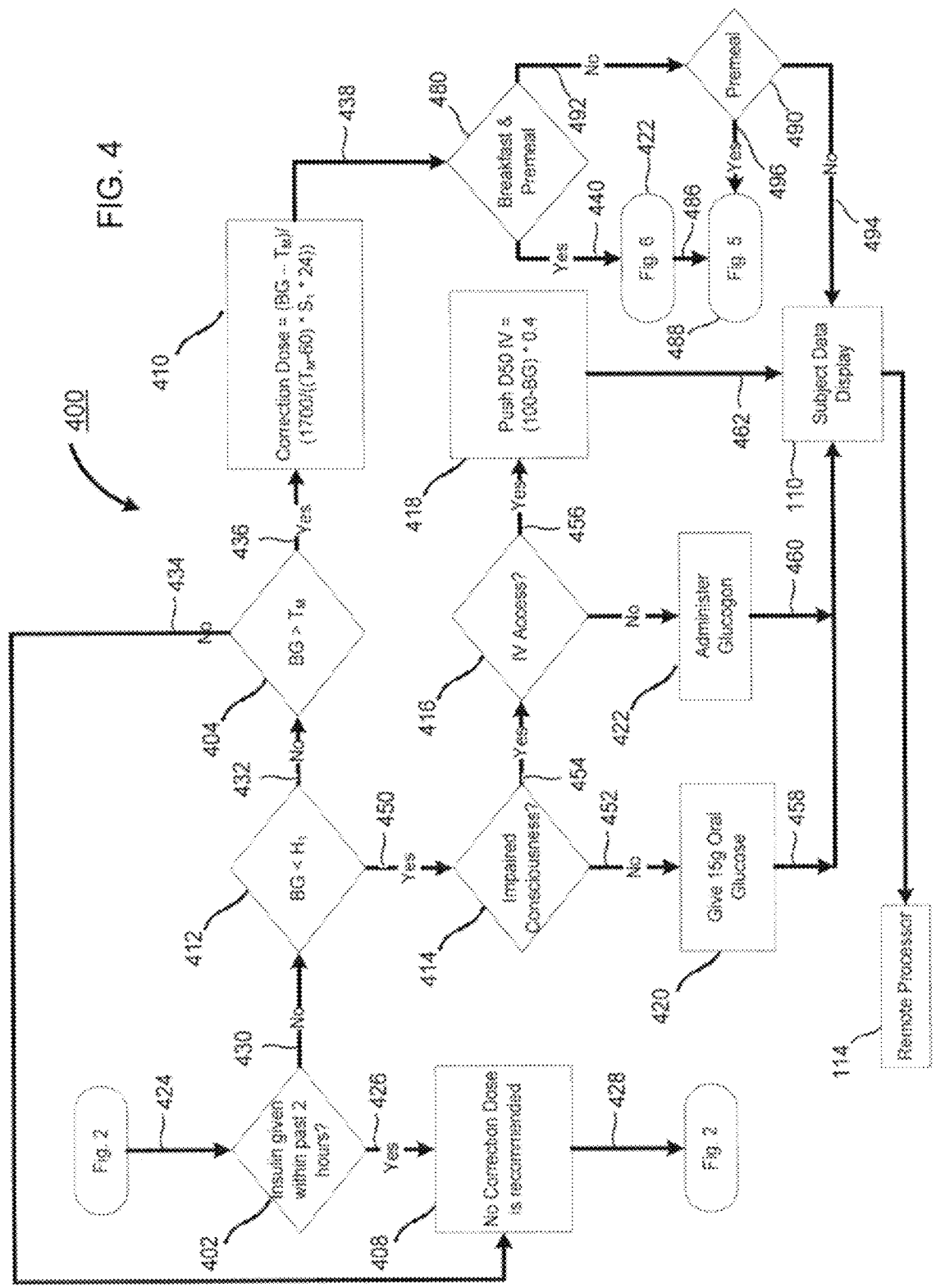
FIG. 4 is a flow block diagram associated with determining a correction dosage to be administered to the subject dependent upon input data provided by the subject associated with the meal type and the time period.

Once an intermediate processing or correction dosage calculation is completed in FIG. 2 for a particular meal type and time period, the logic flows on line 120 (FIG. 1) to dosing adjustment block 108 which is calculated in FIG. 4 to be further detailed and described. Once the dosing adjustment in block 108 has been made by processor 116, information flows on line 122 to subject data display 110 for providing a visual, audio or other type of sensory indication to the subject as to the recommended insulin dosage to be administered. In overall concept, the information provided on line 122 to data display 110 is then transported to remote processor 114 on line 124 for storage of all data calculated. Remote processor 114 stores prior basal dosages, prior administered blood glucose doses (bolus), hypoglycemia threshold, and mid-point target blood glucose range ($T_M$) which are transmitted to processor 116 on line 130 for processing.

Returning back to block 103, which has been detailed in the description of FIG. 3, all information with regard to the physical condition of the subject is additionally transported on line 126 to subject data display 110 simultaneous with the information flowing on line 128 into block 104 for determination of the blood glucose time period.

System processor 116 and subject data display 110 may be incorporated within a standard Personal Computer System which has a standard monitor screen for permitting the subject to visually obtain the recommended insulin dosage value being calculated within the system processor 116 and/or the remote processor 114. The subject display monitor 110 generally provides visual data to the user, however, as is known, audio information may also be transmitted to the subject.

Referring now to FIGS. 2 and 4-7, when the information flows into block 104, the logic initially is directed to FIG. 2 where a decision is made as to whether the time period at which the blood glucose level has been taken is determined to be pre-meal, post-meal, bedtime, mid-sleep, or miscellaneous.

Information flow from within block 104 of FIG. 1 is inserted on line 260 to decision block 202 for determining whether the blood glucose reading taken is pre-meal. If the blood glucose reading is taken prior to breakfast, lunch, dinner, or snack, then information flows on line 262 to decision block 204 to determine whether the meal type of the pre-meal time period is breakfast.

If it is determined in decision block 204 that the pre-meal type is breakfast, then the logic is transported on line 264 to block 212 for calculation of a blood glucose correction dosage or intermediate blood glucose correction dosage. Block 212 includes the processing of the logic blocks in FIG. 4. The information in block 212 is inserted into decision block 402 on line 424 for determination of whether insulin has been administered within a predetermined time period which is generally 2.0 hours, however, this is adjustable by a physician for a specific subject. If insulin has been administered within a predetermined time period, the logic then moves on line 426 to block 408 where "no correction dose" is recommended and the information returns to FIG. 2 for further processing in block 220.

Where insulin has not been administered within a predetermined time period found in decision block 402, information is directed to decision block 412 on line 430 for determination of whether the instant or current blood glucose level reading from the glucometer in block 102 is less than the hypoglycemia threshold value stored in block 114. If the blood glucose reading is equal to or greater than the hypoglycemia threshold value, information is transported on line 432 to decision block 404 where a determination is made whether the blood glucose reading is greater than the mid-point of the target blood glucose range ($T_M$).

If it is determined that the blood glucose reading is less than the mid-point of the target blood glucose range, information is directed on line 434 back to block 408 where there is "no correction dose recommended" and the information flows back to FIG. 2 for further processing on line 428 in block 220.

Where it is determined that the blood glucose reading is greater than the mid-point of the target blood glucose range in block 404, the logic then passes on line 436 to calculation block 410 where the intermediate correction or correction insulin dosage is calculated. The intermediate blood glucose correction dosage calculated in block 410 is a function of the blood glucose reading, the mid-point of the blood glucose target range, and the subject sensitivity factor in accordance with the formula:

$$CD = \frac{(BG - T_m)}{(1700((T_m - 60) \times S_1 \times 24)} \quad (1)$$

Where: CD=correction dose calculated (units of insulin)
BG=blood glucose reading (mg/dl)
$T_m$=mid-point of blood glucose target range (mg/dl)
$S_1$=patient insulin sensitivity factor (units/mg/dl)

Once the blood glucose correction dosage is determined in calculation block 410, information is directed to decision block 480 on line 438. Since the correction dosage and associated logic of FIG. 4 is used in conjunction with all time periods where the blood glucose value is taken including pre-meal, post-meal, bedtime, mid-sleep, and miscellaneous, as well as meal types, breakfast, lunch, dinner, snack, bedtime and mid-sleep, the information on line 438 is inserted into the decision block 480 where it is once again determined whether the meal type and the time period is breakfast and pre-meal.

Figure 5:
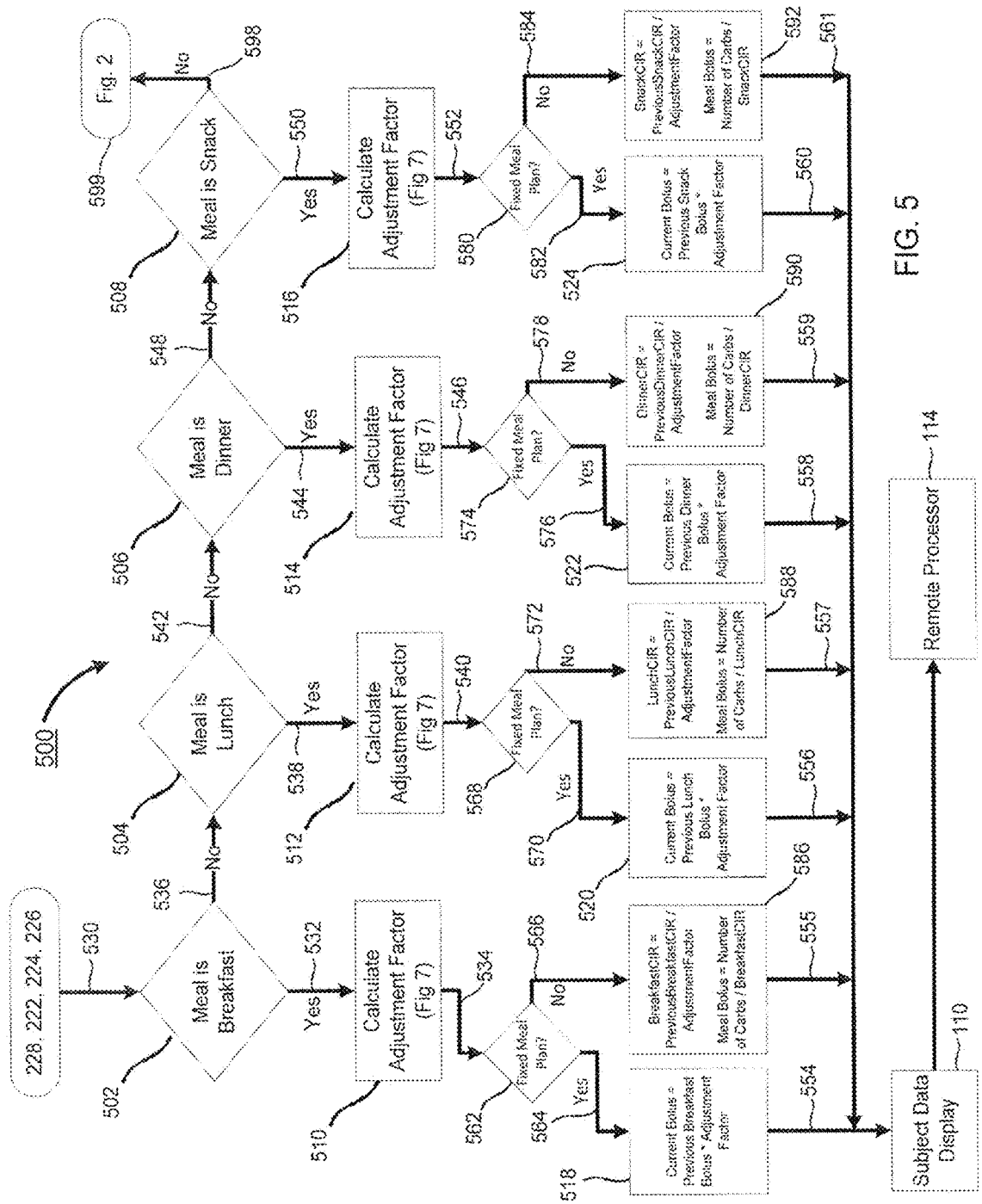
FIG. 5 is a logic flow diagram for calculation of the current bolus associated with an adjustment factor.
Figure 6:
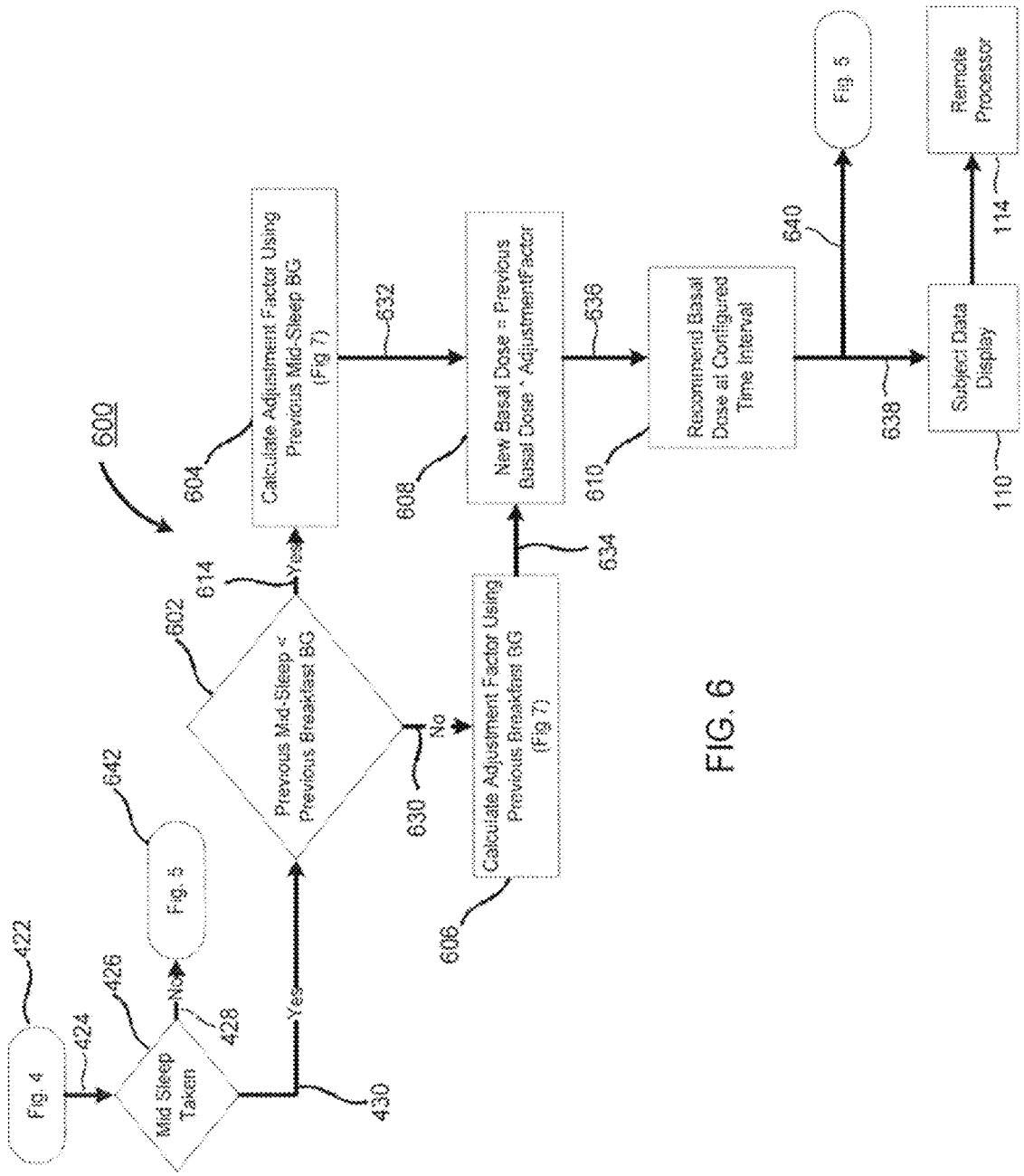
FIG. 6 is a flow block diagram showing the processing for calculating updated basal dosages.

If both of the conditions are met (e.g., meal type is pre-meal and time period is breakfast), information then is directed on line 440 to transfer block 422 which is representative of FIG. 6. Referring now to FIG. 6, information from transitional block 422 passes on line 424 into decision block 426 to determine whether a previous mid-sleep blood glucose level has been determined and stored in either system processor 116 and/or remote processor 114. If there is no previous mid-sleep blood glucose level available or the subject does not take mid-sleep blood glucose readings, information passes on line 428 to transfer block 642 for further processing in FIG. 5.

If there is a previous mid-sleep blood glucose level availability, information is directed on line 430 to decision block 602 to determine whether the previous mid-sleep blood glucose level was less than the previous breakfast blood glucose level reading stored in remote processor 114. If the previous mid-sleep blood glucose level is less than or equal to the previous breakfast blood glucose level, the logic passes on line 614 to calculation block 604 for calculating an adjustment factor using the previous mid-sleep blood glucose level.

Figure 7:
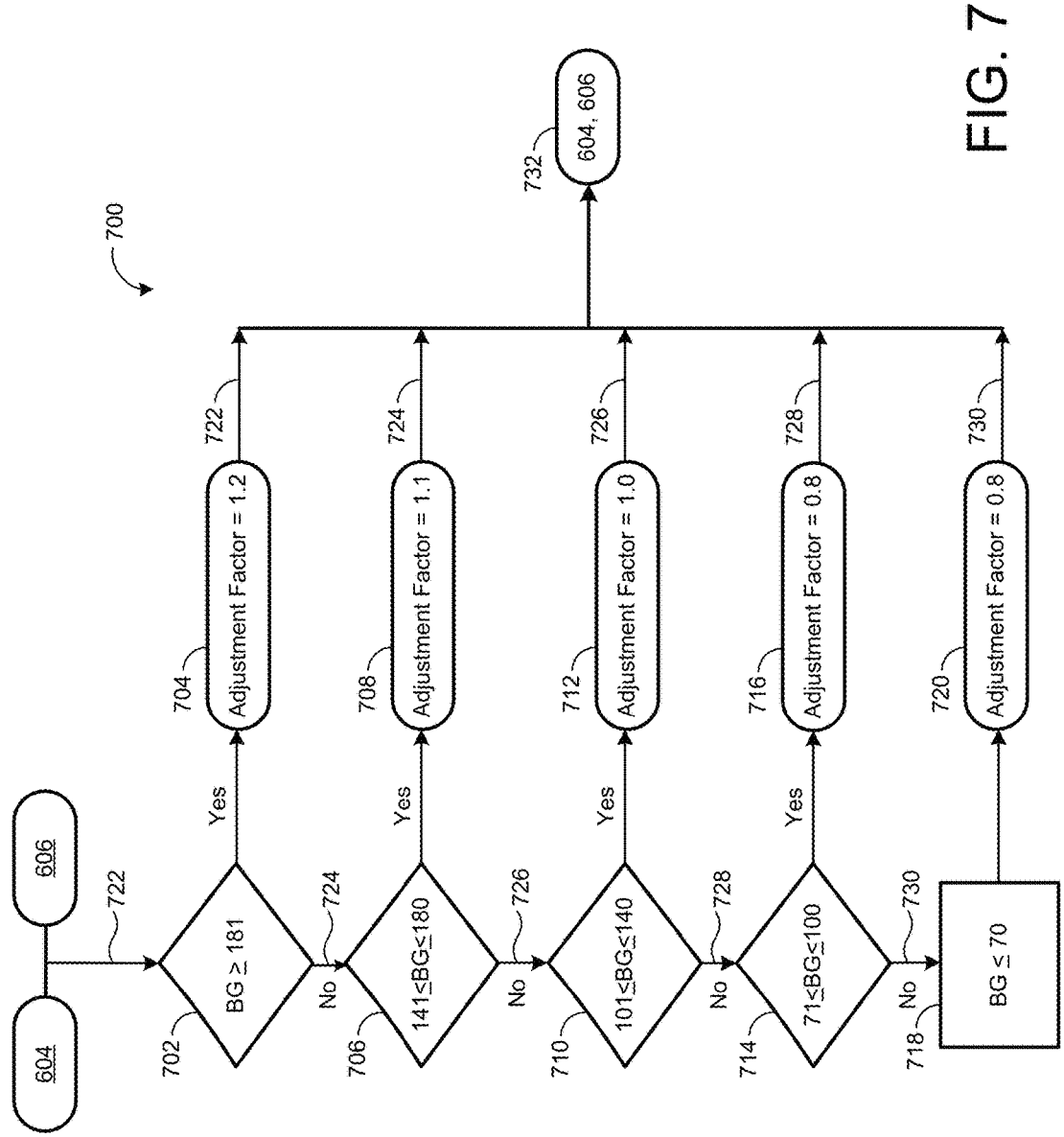
FIG. 7 is a flow block diagram showing the adjustment factor calculations based upon current blood glucose levels.

Calculation of the adjustment factor using the previous mid-sleep blood glucose level is shown in FIG. 7 to be further detailed. Block 604 calculations decision blocks are made in 702, 706, 710, and 714, as well as calculation block 718 which provides for a particular adjustment factor associated with the blood glucose reading. The information is then passed to block 608 in FIG. 6 for a Basal dose to be calculated based upon the adjustment factor.

If the previous mid-sleep blood glucose level is greater than the previous breakfast blood glucose level in decision block 602, information is transported on line 630 to processing block 606 where the adjustment factor is calculated using the previous breakfast blood glucose level in accordance with the adjustment factor found in FIG. 7. Thus, in both processing block 604 and 606, an adjustment factor is calculated in the logic flow associated with FIG. 7.

Calculation blocks 604 and 606 are calculated in FIG. 7 where the information flows on line 722 to initial decision block 702 to determine whether the blood glucose level is greater than or equal to 181 mg/dl. If the blood glucose level is greater than 181 mg/dl, then an adjustment factor is set in block 704 as being 1.2. If the blood glucose level is not greater than or equal to 181 mg/dl, then information flows on line 724 to decision block 706 where it is determined whether the blood glucose level is within the range of 141 mg/dl to 180 mg/dl. If the blood glucose level is within the range defined in decision block 706, the adjustment factor is set to be 1.1 in block 708. If the blood glucose level is not within the range determined in decision block 706, information is transported on line 726 to decision block 710 where it is determined whether the blood glucose level is greater than or equal to 101 mg/dl and less than or equal to 140 mg/dl. If the blood glucose level is within the range defined in block 710, the adjustment factor is set in block 712 as 1.0. If the blood glucose level does not fall within the range associated with decision block 710, information is directed on line 728 to decision block 714 where it is determined whether the blood glucose level is within the range of 71 mg/dl to 100 mg/dl. If the blood glucose level is within the range defined in block 714, the adjustment factor is set in block 716 to be 0.8. If the blood glucose level is not within the range associated with the decision made in decision block 714, the blood glucose level must be less than or equal to 70 mg/dl as shown in block 718 and in this case, the adjustment factor is set in block 720 as 0.8. The adjustment factors set in blocks 704, 708, 712, 716, and 720 are dimensionless.

Once the proper adjustment factor is defined in blocks 704, 708, 712, 716, or 720 information flows on respective lines 722, 724, 726, 728, or 730 to transfer block 732 where information returns to either blocks 604 or 606 in FIG. 6.

As stated, the adjustment factor after being calculated in FIG. 7, the information returns to FIG. 6 and in particular to blocks 604 and 606. The information in block 604 and 606 respectively pass on lines 632 or 634 to calculation block 608 where the new basal dose is calculated. The new basal dose calculated in block 608 is the previous basal dose multiplied by the adjustment factor and this value is inserted into block 610 to recommend the basal dose at the configured time interval. Information then flows on line 636 to block 638 to insert the recommended basal dose to the subject data display 110 and storage in the system processor 116 and/or remote processor 114, as well as being returned on line 640 for further calculations of either the breakfast, lunch, dinner, or snack bolus associated with the logic flow in FIG. 5.

Thus, as shown in FIG. 4, if it is determined that both conditions of the time period being pre-meal and the meal type is breakfast, information is passed on line 440 to transfer block 422 for calculations in FIG. 6 and then the information is inserted into transfer block 488 for processing in accordance with the logic described in FIG. 5.

Returning now to FIG. 4, where once the correction dosage has been calculated in block 410, and the information passed to decision block 480, if it is determined in block 480 that both conditions of the time period being pre-meal and the meal type being breakfast are not met, logic flows on line 492 to decision block 490. Decision block 490 determines whether the time period is pre-meal. If the time period is pre-meal the logic moves on line 496 to transfer block 488 for processing in FIG. 5. If the time period is not pre-meal then the logic flow is directed to block 110 in FIG. 1 and the correction dose is inserted in accordance with the calculations made in calculation block 410.

Returning back to FIG. 4 and decision block 412, if it is determined in decision block 412 that the blood glucose level is less than the hypoglycemia threshold level, information flows on line 450 to decision block 414. In decision block 414, it is determined whether the subject has impaired consciousness, and if the subject does not have impaired consciousness information flows on line 452 to block 420 where the subject is instructed to be given a predetermined dosage of oral glucose and data is then sent directly to data display block 110. If the subject has impaired consciousness found in decision block 414, information flows on line 454 to decision block 416 where it is determined whether there is IV access. If there is IV access, information on line 456 is inserted into block 418 where instructions are provided to give a D50IV=(100−BG)×0.04 amount to the subject. If there is no IV access, glucogen is then recommended to be administered in block 422. Information from blocks 420, 422, and 418 are passed on lines 458, 460, and 462 for information input to data display 110 and subsequently inserted into remote processor 114 of FIG. 1.

Returning now to FIG. 2, once the basal dose has been adjusted in block 220 as associated with the processing in FIGS. 6 and 7, for a time period which is pre-meal and a meal type which is breakfast, information is directed to block 228 for calculation of the recommended insulin dosage at breakfast or breakfast bolus.

Similarly, if the time period is pre-meal and meal type is lunch, calculations of the intermediate blood glucose correction dosage for lunch is calculated in FIG. 4. If the time period is pre-meal and the meal type is dinner, calculation of the intermediate blood glucose correction dosage is made in block 216. Similarly, if it is determined that the time period is pre-meal and that the meal type is a snack in decision block 210, a calculation of the blood glucose correction dosage for the snack is calculated in block 218.

In all processing and calculation blocks 212, 214, 216, and 218, the calculations are provided in association with the previous logic flow description given for the logic blocks in FIG. 4.

Information from FIG. 2 processing blocks 228, 222, 224, and 226 are calculated in accordance with the logic flow in FIG. 5. Calculation of the breakfast, lunch, dinner, or snack bolus is shown in FIG. 5 with information passing from blocks 228, 222, 224, and 226 on line 530 to decision block 502 where it is once again determined whether the pre-meal time period is breakfast. If the pre-meal time period is breakfast, information passes to calculation block 510 on line 532 for calculation of the adjustment factor as previously detailed in the logic flow provided for FIG. 7.

If the time period is pre-meal and the meal type is breakfast, calculation of the adjustment factor is made in block 510 in accordance with FIG. 7 as previously discussed. Information then passes to decision block 562 where there is a determination of whether the subject is on a fixed meal plan. If it is determined that the subject is on a fixed meal plan, such as substantially the same number of carbohydrates to be ingested at each time period and meal type, information then passes on line 564 to calculation block 518 which calculates the current bolus in accordance with the equation:

$$CB = CB_i \times AF \quad (2)$$

Where:
CB=current bolus (units of insulin)
$CB_i$=previous bolus administered at the previous Meal type and time period (units of insulin)
AF=adjustment factor (dimensionless)

The current bolus is then passed on line 554 to subject data display 110 and eventually to remote processor 114 as provided in FIG. 1. If it is determined that the subject is not on a fixed meal plan in decision block 562, information is directed through line 566 to calculation block 586 where a number of calculations are performed. Initially, the total prescribed daily basal dose of insulin in units of insulin per day is calculated (TDD) in accordance with the formula:

$$TDD = TDD_m \times W_S \quad (3)$$

Where:
TDD=total prescribed daily basal dose of insulin (units of insulin)
$W_S$=weight of subject (Kg.)
$TDD_M$=subject's Total Daily Dose Multiplier (a weighting factor having dimensions of (units per Kg/day). Typically 0.25 for pediatric subjects, 0.3 for subjects with renal insufficiency, 0.5 for adult subjects, or another subject specific number)

Once the total prescribed daily basal dose is calculated in equation (3), within block 586, the meal of bolus (CB) is calculated by first calculating the carbohydrate to insulin ratio (dimensionless) in accordance with the formula:

$$CIR = 450 \times TDD \quad (4)$$

Where: CIR=current carbohydrate to insulin ratio (dimensionless)
TDD=total prescribed basal dose of insulin (units of insulin)

Using the previous selected pre-meal CIR to calculate the instant CIR for a particular meal type is made in accordance with the formula:

$$CIR_{B,L,D,S} = \frac{CIR_{P_{B,L,D,S}}}{AF} \quad (5)$$

Where: $CIR_{B,L,D,S}$=instant carbohydrate to insulin ratio for a selected meal type of breakfast, lunch, dinner, or snack
$CIR_{B,L,D,S}$=previous carbohydrate to insulin ratio for previous selected meal type of breakfast, lunch, dinner or snack
AF=adjustment factor Finally, the current bolus to be recommended is derived from the Equation:

$$CB = \frac{C_{EST}}{CIR_{B,L,D,S}} \quad (6)$$

Where:
$C_{EST}$=estimated number of carbohydrates to be ingested at the pre-meal time period for the current meal type (mg.)
$CIR_{B,L,D,S}$=calculated carbohydrate to insulin ratio calculated in Equation 5

Subsequent to the calculation of the current bolus in block 518 or block 586, information passes on respective lines 554 and 555 to subject data display 110 and then to remote processor 114.

If it is determined in decision block 502 that the meal is not breakfast, information is directed on line 536 to decision block 504 where a decision is made as to whether the meal is lunch. If the pre-meal is lunch, then information is passed on line 538 to calculation block 512 for calculation of the adjustment factor in FIG. 7 as previously discussed. Once the adjustment factor has been determined from the logic flow in FIG. 7, information then is transported on line 540 to fixed meal plan decision block 568. Decision block 568, similar to decision block 562, determines whether the subject is on a fixed meal plan and if the subject is on a fixed meal plan, information passes on line 570 to calculation block 520 where the current bolus is calculated in accordance with Equation 2. Where the subject is not on a fixed meal plan as determined in decision block 568, information passes on line 572 to calculation block 588 which calculates the lunch bolus in accordance with Equations 3, 4, 5 and 6 as previously discussed. Subsequently, information passes either on line 556 or 557 to subject display data 110 and remote processor 114.

If it is determined that the meal type is not lunch in decision block 504, information is transported on line 542 to decision block 506 where it is determined whether the meal type is dinner. If the meal type is dinner, information is inserted to calculation block 514 on line 544 for calculation of the adjustment factor provided by the logic in FIG. 7. Once the adjustment factor in FIG. 7 has been calculated, information passes on line 546 to decision block 574 determining whether the subject is on a fixed meal plan. The decision block 574 is similar to decision blocks 562 and 568. If it is determined that the subject is on a fixed meal plan, information is then sent to calculation block 522 on line 576 for calculation of the current bolus (CB) in accordance with Equation 2. If the subject is not on a fixed meal plan as determined in decision block 574, the information enters calculation block 590 for calculation of the dinner meal bolus in accordance with Equations 3, 4, 5 and 6. Information is then sent from either calculation block 522 or block 590 on respective lines 558 and 559 to subject data display 110 and then to remote processor 114.

If it is determined in decision block 506 that the meal is not dinner, information then flows on line 548 to decision block 508 where it is determined whether the meal type is a snack. If it determined in decision block 508 that the meal is a snack, information passes on line 550 to calculation block 516 where the adjustment factor is calculated in accordance with FIG. 7. Information then passes on line 552 to decision block 580 which determines whether the subject is on a fixed meal plan. If the subject is on a fixed meal plan as determined in decision block 580, information passes on line 582 to calculation block 524 where the current bolus is calculated based upon equation 2. If the subject is not on a fixed meal plan, the logic flows through line 584 to calculation block 592 where the current meal bolus is calculated in accordance with Equations 3, 4, 5, and 6. Information from block 524 or block 592 is then transported on either Line 560 or 562 to subject data display system 110 and then to remote processor 114.

In this manner, when the blood glucometer reading is taken as represented by block 102, and the physical condition is input by the subject as represented by block 101, when the time period of the blood glucose reading is taken is pre-meal as is determined in decision block 202, a breakfast, lunch, dinner, and snack bolus is calculated by system 100.

If the meal type is not a snack, then the time period is miscellaneous and passes on line 598 to transfer block 599 where logic is transferred to line 288 in FIG. 2. Processing is then provided in calculation block 258 in accordance with the logic flow in FIG. 4.

Returning to FIG. 2, assuming that the blood glucose time period has been determined not to be a pre-meal time period in decision block 202, the information passes on line 280 to decision block 230 where decision block 230 determines whether the time period is a post-meal time. If the time period is determined to be post-meal, information is transported on line 282 to decision block 232 where a decision is determined whether this is a breakfast post-meal glucometer reading. If the inputs provided by the subject is to a time period which is post-meal and the meal type is breakfast, information is then transmitted to calculation block 240 in FIG. 2. In this instance, there is no adjustment of the basal dose as was the case when the time period was pre-meal (previously described) and the meal type was breakfast.

Calculation block 240 directs the information to FIG. 4 where a correction dose is calculated in calculation block 410. All logic blocks have been previously detailed, however, in overview, if insulin has not been given within a predetermined period of time, for example two hours as indicated in decision block 402, and the blood glucose reading is equal to or greater than the hypoglycemia threshold value ($H_1$) as determined in decision block 412, the information is directed to decision block 404 and if the blood glucose reading is determined to be greater than the midpoint target blood glucose range reading, the correction dose is calculated in calculation block 410. Responsively, subsequent to the calculations provided in calculation block 240, the results and calculation of the post-meal breakfast correction is transmitted on line 284 to subject display 110 and remote processor 114 for storage of the data calculated.

Similarly, as has previously been described for the pre-meal type calculations in decision blocks 206, 208, and 210, a decision is made as to the fact whether the post-meal blood glucose reading is taken subsequent to lunch in decision block 234, dinner in decision block 236, or a snack in decision block 238. If it is determined that the post-meal blood glucose reading is subsequent to lunch in decision block 234, the information then is inserted into calculation block 242 for calculation of the post-meal lunch correction as associated with the logic flow previously described for FIG. 4.

If the decision in decision block 234 is that the post-meal was not lunch, the information then is directed to decision block 236 for determination of whether the post-meal blood glucose reading was dinner and if it is dinner, the logic flows to block 244 and correction dosage as well as the subject meal bolus is made in association with FIG. 4.

If the blood glucose post-meal reading is a snack determined in decision block 238, similarly as previously described, the information is directed to calculation block 246 for calculation in the same manner as previously described for the post-meal breakfast, lunch and dinner decisions. Information from blocks 240, 242, 244, and 246 are then provided on line 284 to both subject display 110 and remote processor 114 for storage of the data and display of the recommended correction reading.

If it is determined in decision block 230 that the blood glucose time period is neither a pre-meal nor a post-meal, the information is directed on line 290 to decision block 248 where it is determined whether the blood glucose taken is at the time period of bedtime (prior to sleep).

With the blood glucose reading provided in block 101, the information is directed to calculation block 254 for insert into the logic flow of FIG. 4. The logic in FIG. 4 in overall view, passes into correction dose calculation block 410. The bolus for bedtime is then provided on line 286 (FIG. 2) to both subject display system 110 and remote processor 114 as shown in FIG. 1.

Assuming that the blood glucose type is not found to be bedtime in decision block 248, information is then inserted on line 292 to decision block 250 where the blood glucose reading time period is taken as "mid-sleep". If the blood glucose reading is taken as a mid-sleep type reading, information then is inserted into calculation block 256 where the calculation correction is transmitted to the logic previously detailed for FIG. 4 and then inserted on line 286 to subject display system 110 and remote processor 114 as shown in FIG. 2.

In the event that the blood glucose reading provided in block 101 is not a mid-sleep reading as determined in decision block 250, the information then passes on line 294 to calculation block 252 where the meal type is defined as miscellaneous since it is neither for a breakfast, lunch, dinner, or snack reading. The information in 252 is then directed to calculation block 258 where the bolus is calculated in accordance with FIGS. 4, 5, and 7.

In the event that the blood glucose reading meets the time criteria period of a pre-meal, but is not at breakfast, lunch, dinner, or snack as determined in decision blocks 204, 206, 208, and 210, then the meal type must be "miscellaneous" and the information passes on line 288 into block 252 and 258 for calculation of the correction dosage. As seen in FIG. 2, if the blood glucose reading is post-meal, but is not for breakfast as determined in decision block 232, lunch as determined in decision block 234, dinner as determined in decision block 236, or the snack as determined in decision block 238, again, the information is directed on line 288 to 252 since the reading must be a "miscellaneous" reading. In all cases subsequent to the bolus being determined in 254, 256, and 258, information calculated is then inserted for display in system display 110 and stored in remote processor 114 for further use.

In overall concept, there is provided in FIGS. 1-7 a system for determining the insulin dosage value to be administered to a subject dependent on many interrelated parameters. Input to system 100 includes a glucometer reading taken by the subject at a time period defined by whether the blood glucose reading is taken pre-meal, post-meal, bedtime, or at some miscellaneous time. Remote processor 114 maintains in storage, prior basal dosages, hypoglycemia thresholds, target ranges and mid-points of target ranges, and subject insulin sensitivity factor. The subject provides a manual input on line 118 as represented by block 105 as to the particular time period, whether such is pre-meal, post-meal, bedtime, or at some miscellaneous time. Additionally, the meal type such as breakfast, lunch, dinner, or snack is inserted as represented by block 105 for insert into processor 116 for determination of the appropriate correction factors and bolus to be calculated.

System 100 provides the patient with calculated insulin dosage instructions based on nutritional and physical information, as well as personal history of insulin administration and resulting blood glucose levels as previously described. The calculated insulin dosage instructions are output to the subject on subject data display 110 which can be the monitor of a PC or through some other type of audio or sensory indication to the subject. The resulting data is then inserted into remote processor 114 for storage of the data where prior basal dosages, prior blood glucose doses, hypoglycemia thresholds, subject insulin sensitivity factor, whether a meal plan is in effect, and mid-point of target ranges are maintained in storage.

Once the user has manually input the current glucometer reading of his/her blood glucose level from block 102 along with the time period and meal type as represented in block 105, the subject further includes input as to a physical condition from block 101. All of this data is then inserted into processor 116 where the physical condition is initially calculated independent of the further processing to be accomplished by processor 116. The physical condition may require administration of a predetermined amount of carbohydrates as calculated in FIG. 3 for each time period of exercise which has been accomplished or is being planned and such is inserted into subject data display 110. Prior basal dosages and prior BG doses of the subject for previous time periods of pre-meal, post-meal, bedtime, or miscellaneous as well as prior BG doses associated with specific time periods and meal types is stored in remote processor 114 along with the hypoglycemia threshold and the mid-point of the target range ($T_m$). All of this is inserted into processor 116 on line 124 for calculations in blocks 104 and 108.

System 100 then processes all data drawing on the preset conditions and subject history for determining optimum dosage levels of the subject's current condition where all calculated data is then displayed as represented by block 110 and the calculated data is then stored in remote processor 114.

FIG. 2 is representative of the calculation blocks 104 and 108 in a further breakdown of the processor calculation procedures. The system 100 processes patient input of dietary events in FIG. 2 where initially the subject indicates whether the current blood glucose level read from glucometer reading 102 is a time period of a pre-meal (decision block 202), post-meal (decision block 230), prior to bedtime (decision block 248), or mid-sleep cycle (decision block 250). If the time period is neither pre-meal, post-meal, bedtime, or during the mid-sleep cycle, then the time period is miscellaneous as represented by input block 252. Thus, all time periods are then represented and appropriate calculations can be processed. Each of the decision blocks 202, 204, 206, 208, 210 or 203, 232, 234, 236, 238, or 248 and 250 define individual series of decision blocks. A positive indication for one decision block implies a negative indication for other decision blocks in each series. This type of event oriented organization permits the subject to expeditiously enter important information.

If the time period is pre-meal as determined in decision block 202, the patient elects or indicates whether the pre-meal reading is breakfast as shown in decision block 204. As previously described, if the pre-meal is not breakfast, the election is made for lunch in decision block 206, dinner in block 208, or a snack in decision block 210. An algorithm within processor 116 calculates the dosage correction for the planned meal using the calculation algorithm as previously described in FIG. 4 in association with sub-algorithms provided in FIGS. 5-7 and in overall block diagram shown in blocks 212, 214, 216, and 218 of FIG. 2.

In the time period of pre-meal and breakfast, the basal dose is adjusted as indicated in block 220 in association with the logic flow shown in FIG. 6.

For all pre-meals such as breakfast, lunch, dinner, snack, or miscellaneous, the pre-meal bolus or recommended insulin dosage is calculated in associated blocks 228, 222, 224, and 226. If the meal type is neither breakfast, lunch, dinner, or a snack, then it is defined as a miscellaneous time period and the calculations for the bolus are input into block 252 and the calculated correction is made in block 258 as previously detailed. All recommended optimum doses to be taken in any of the time periods is then displayed to the subject on display 110 and the data inserted into remote processor 114 for further use for subsequent blood glucose readings at specific meal types and time periods.

Mealtime nutritional information may be input by the subject and a post-meal bolus correction is calculated for correcting unacceptable blood glucose levels within the logic of processor 116 as indicated by block 108 in FIG. 1 in association with FIG. 5. logic.

In the event that the time period of the blood glucose reading is post-meal and determined in decision block 230, once again the meal type is determined from the decision blocks 232, 234, 236, or 238 for respective calculation of the post-meal type correction in respective blocks 240, 242, 244, and 246. Each of the decision blocks 230, 232, 234, 236, and 238 determine a series of decision blocks where a positive indication for one decision block defines a negative indication for other decision blocks in this series.

As shown in FIG. 2, if the time period is bedtime as determined in decision block 248, a pre-sleep blood glucose correction dose is calculated in calculation block 254 associated with calculations performed in the logic steps as provided in FIG. 4. In the event that the blood glucose reading is mid-sleep as determined in decision block 250, where it has been determined in decision block 248 that the time period is not bedtime, the logic blows into decision block 250 where it is determined whether the time period is mid-sleep and if the time period is mid-sleep, calculations are made in block 256 in accordance with the logic flow in FIG. 4. All information is then inserted on line 286 for insert into subject display 110 and remote processor 114.

In the event that one of the meal types previously discussed are found for either the pre-meal, post-meal, mid-sleep or bedtime calculations, the meal type is defaulted to input block 252 where it is determined that the meal type is miscellaneous and then passes to calculation block 258 for calculation in accordance with the calculations processed in FIG. 4. Once again, the information from block 258 is inserted onto line 286 for display and storage of the data in respective blocks 110 and 114. As previously discussed, if the information exiting decision blocks 210 and 238 indicate that the meal type was neither breakfast, lunch, dinner, or a snack, the information is directed to input block 252 and then inserted into block 258 for calculation in accordance with the logic associated with FIG. 4.

FIG. 4 is a sub-system which takes information from FIG. 2 and is associated with the calculation blocks 212, 214, 216, and 218 for the pre-meal blood glucose reading time period, as well as logic blocks 240, 242, 244, and 246 for the post-meal time period and blocks 254, 256, and 258 for the time periods of bedtime, mid-sleep or miscellaneous. The calculation blocks of FIG. 2 are read into decision block 402 for determination of whether insulin has been administered within a predetermined time interval of the taking of the blood glucose reading and if insulin has been given within this predetermined time, there is no correction dosage recommended by system 100 and the information is returned to FIG. 2 for further processing.

If the insulin has not been given within the predetermined period of time (which is generally two hours), it is determined in decision block 412 whether the subject's blood glucose level is below a pre-set hypoglycemia risk level ($H_1$) (hypoglycemia threshold). If it is not below the $H_1$, information then is directed to decision block 404 where it is determined whether the blood glucose reading is greater than the mid-point of the target range and if it is not, information is then sent back to block 408 where no correction dose is recommended and the system returns to FIG. 2.

If the blood glucose reading is greater than the mid-point of the target range as determined in decision block 404, the information then is directed to block 410 where a correction dosage is calculated as previously discussed in relation to the correction dosage equation. The correction dosage is then inserted into decision block 480 where it is determined whether the time period is pre-meal and whether the meal type is breakfast. If the data corresponds to both of these two criteria, the information is then inserted into FIG. 6 for calculation of the recommended basal dose based upon previous mid-sleep blood glucose levels and adjustment factors in FIG. 7. The logic then flows on line 486 to FIG. 5 as shown by transfer block 488. If the information does not correspond to both a breakfast and pre-meal time period in decision block 420, the information then goes directly to FIG. 5 for further calculations as previously discussed.

In overall concept, if the decision in decision block 412 determines that the blood glucose level is below $H_1$, the system requests input in decision block 414 regarding the consciousness of the subject. If consciousness is not impaired, the data then flows to block 420 for administration of a predetermined amount of oral glucose (generally 15 grams). If the subject does have impaired consciousness, the physician or caregiver is then instructed to either administer glucogen in block 420 or if there is IV access, for intravenous insertion of an insulin based upon a 50% saline solution and insulin in accordance with the previously defined equations.

Sub-system 500 shown in FIG. 5 illustrates the logic flow within processor 116 associated with adjustment factors calculated in sub-system 700 shown in FIG. 7 which are incorporated into the meal time bolus calculations in the respective calculation blocks 228, 222, 224, and 226 of FIG. 2. For respective meal types, calculation adjustment factors are calculated in the logic flow of FIG. 7 and then the current bolus is calculated as a function of the previous meal type bolus times the adjustment factor for each of the meal types in respective blocks 518, 520, 522, and 524 as well as a determination of whether the subject is on a meal plan. Information is then sent to subject display 110 and remote processor 114 subsequent to the calculations made.

Sub-system 600 shown in FIG. 6 describes the system 100 processing for incorporating the patient's personal fasting glucose levels into the adjustment factor (FIG. 7) for an increased defective recommended basal dose. A determination is made if it is determined that this is a breakfast and pre-meal meal type and time period in FIG. 4, the information is sent to block 422 where it then is transmitted on line 424 to the decision block 426 to determine whether a mid-sleep glucose level has been taken and in decision block 426 and if it has not, such returns to FIG. 2 for calculation of the breakfast bolus in calculation block 228. If the mid-sleep glucose level has been taken, the adjustment factor it is determined whether the previous mid-sleep blood glucose level is less than the previous breakfast blood glucose level in decision block 602 and if it is then the adjustment factor is calculated in block 604 from the adjustment factors in FIG. 7. If the previous mid-sleep blood glucose level is equal to or greater than the previous breakfast blood glucose level, then the adjustment factor is calculated from FIG. 7 in block 606 and in this case, the adjustment factor is calculated using the previous breakfast blood glucose level. In either cases, information flows from either block 604 or 606 into block 608 on respective lines 632 and 634 for calculation of the new basal dosage being the previous basal dose multiplied by the adjustment factor. Once again, the recommended basal dose at a particular time period is then provided in data block 610 which is then again sent to the subject display 110 and remote processor 114 as well as back to insertion into the system in FIG. 5.

For a diabetic patient to receive the benefits associated with the use of a special app placed into that patient's smart phone, which app is called the "GlytApp," he or she would follow the method described below starting when that patient would visit the doctor's office. Whenever the word "physician" or "doctor" is used herein, it shall also include other medical professionals who would work with a physician such as a nurse, physician's assistant, medical technician, etc.

Method to Maintain Confidentiality for a Patient Obtaining the GlytApp

1. The doctor decides that he wishes to give his patient a prescription to obtain the app (the GlytApp) for that patient's smart phone for optimum glycemic control.

2. The doctor tells the patient that he would like to prescribe the GlytApp if the patient has a smart phone and is willing to pay a fee to improve his/her glycemic control.

3. If the patient agrees to this arrangement, then the following actions take place.

4. The doctor then requests a serial number for his patient from the company that operates the remote computer system that can communicate with that patient by means of the GlytApp.

5. When the doctor provides the patient's name to the company, the doctor receives over the Internet an appropriate serial number that appears on the doctor's computer. For example, a patient named William E. Jones could get the serial number WJ-000-012. The two letters would be used for those patients who have the initials WJ. So this serial number would be for the $12^{th}$ patient with the initials WJ that is enrolled to receive the GlytApp.

6. The doctor and the remote computer system that communicates with the patient then uses that patient's serial number in all communications between the doctor, the patient, the company and the remote computer system in order to maintain the confidentiality of all medical information pertaining to that patient.

Once the doctor has confirmed with the patient that he/she wants the GlytApp, and the doctor has used the novel method described above to obtain a unique serial number for that patient, then the doctor will fill out on his computer a prescription form as shown in FIG. 8. After it is filled out by the doctor, this form would be sent over the Internet to the company that is providing the GlytApp for that patient. The goal of the form shown as FIG. 8 is to provide advice for the patient that will be displayed on the patient's smart phone and will also be available to the company that will monitor that patient's blood glucose level. This form would appear on the patient's smart phone if and only if that patient was in a state of either hypoglycemia or hyperglycemia. FIG. 8 also constitutes the prescription that an authorized medical professional would use to allow the company to work with that patient.

An important purpose of the prescription form shown in FIG. 8 is that it tells the patient what to do if various levels of hypoglycemia or hyperglycemia occur. Although this form shows certain treatments that are suggested for hypoglycemia and hyperglycemia, the doctor can retain the prerogative to make unique suggestions as to the information on this form depending on what that doctor feels is an optimum response for hypo- or hyperglycemia depending on the needs of a specific patient.

Figure 9:
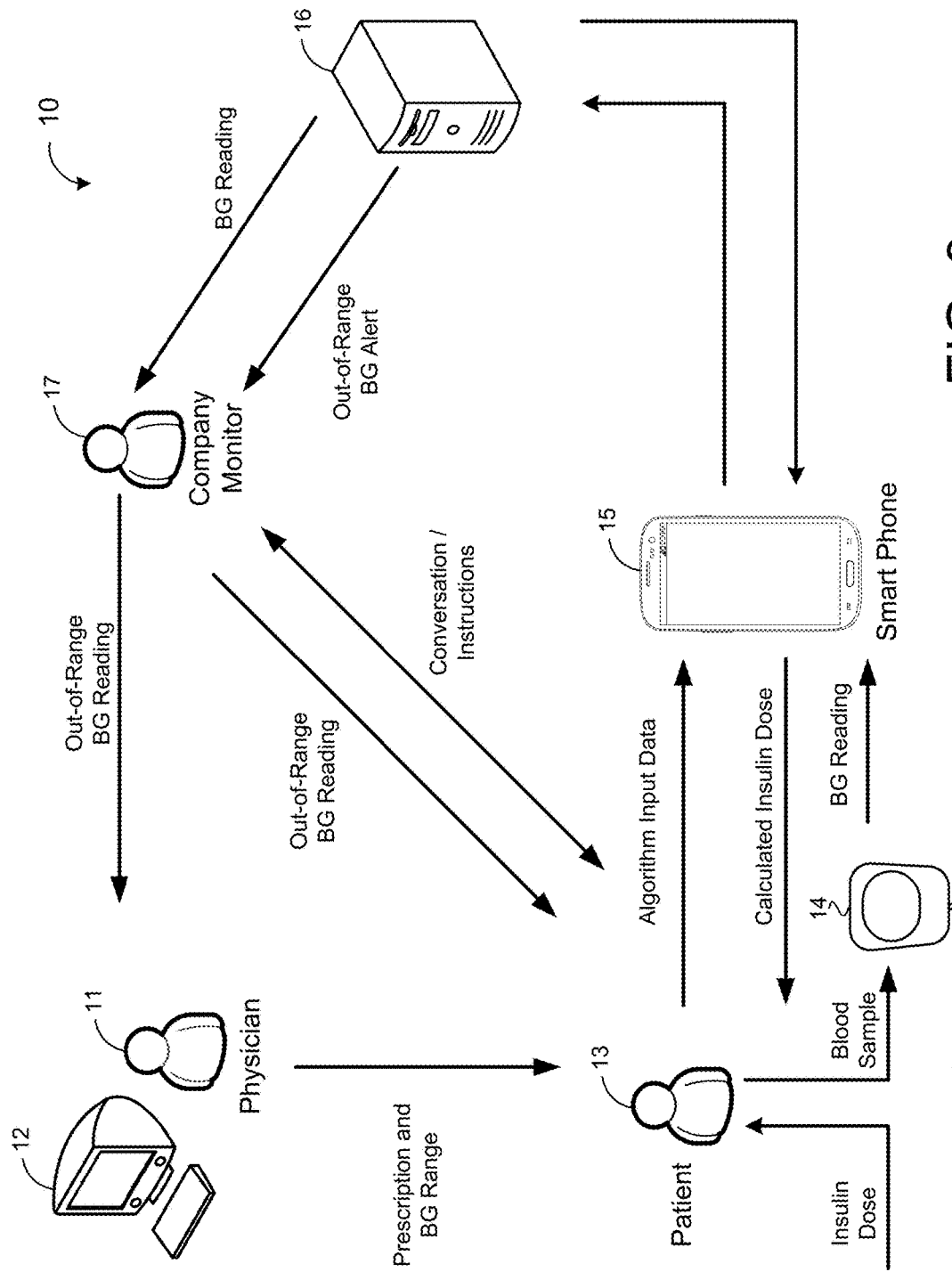
FIG. 9 is a system diagram for a novel system to improve glycemic control for diabetic patients by using a remote computer system in communication with that patient's smart phone.

FIG. 9 is a block diagram of a glycemic control system 10 of the present disclosure to optimize glycemic control for a diabetic patient 13. After the patient 13 has agreed to obtain the GlytApp as described above, the physician 11 uses his computer 12 and the method described above with the assistance of FIG. 8 to set (with the assistance of the company) the GlytApp into the patient's smart phone 15. As shown in FIG. 8, this is accomplished by the physician 11 sending a Prescription and BG Range to the patient 13 which is the filled out form shown in FIG. 8. The filled out form shown in FIG. 8 is sent to the company by the physician 11 and the company sets it into the smart phone 15 of the patient 13.

Figure 13:
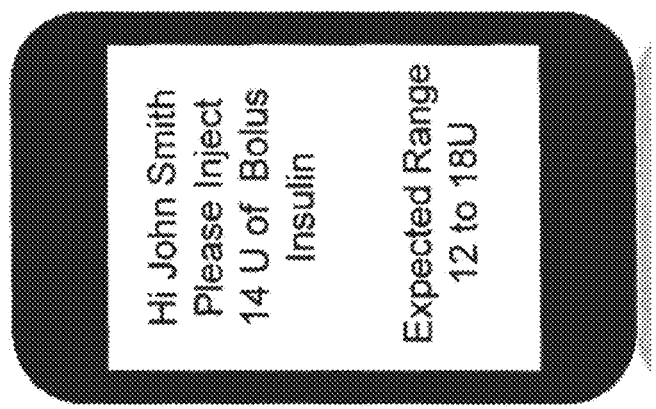
FIG. 13 shows the display of the smart phone that would be received from a remote computer system that indicates the number of units and the type of insulin to be injected into that patient based upon a measured level of blood glucose that the patient placed into that smart phone. Additionally it indicates the expected range for the amount of insulin that has been suggested on prior occasions for approximately the same parameters including blood glucose reading and ingestion of food so that the patient can see if the number of units that is presently suggested for insulin injection is within that expected range.

When the patient 13 provides a Blood Sample onto a paper strip that is read out by the blood glucose meter 14, that blood glucose meter 14 will indicate the patient's level of blood glucose. The patient 13 then calls up the GlytApp and uses it to place the value of that patient's blood glucose into the smart phone 15. The patient 13 would then also put into his/her smart phone 15 other pertinent data as requested by the GlytApp such as: 1) the type and quantity of food that the patient is about to eat; 2) the type and quantity of food that the patient has just eaten; 3) the extent of any exercise that the patient is about to undergo; 4) whether or not the patient is having a menstrual period; 5) the extent to which the patient is having a specific level of stress; 5) the fact that the patient is about to go to sleep; 6) the fact that the patient has just been awakened from sleep; 7) if the patient has a fever and if so, the extent of that fever; 8) if the patient has had any recent changes in circadian rhythm (jet lag); 9) any other factor that has been shown to affect a particular patient's need for insulin. The collection of these data and the measured level of blood glucose as shown in FIG. 13 are then placed into the patient's smart phone 15 and they are indicated in FIG. 9 as the Algorithm Input Data that is sent to the remote computer system 16. Once any of these potentially pertinent data entries have been placed into the GlytApp, these data are then sent by a specific action of the patient 13 on his smart phone 15 to the remote computer system 16. These data constitute the Algorithm Input Data from the patient to the GlytApp and also into the remote computer system 16 as shown in FIG. 9. Based on the patient's prior history that is stored in the memory of the remote computer system 16, for each unique patient serial number, the remote computer system then sends the Calculated Insulin Dose (as seen in FIG. 9) to the patient's smart phone 15. When that data is seen on the patient's smart phone 15, he/she injects an Insulin Dose as indicated in FIGS. 9 and 13. The remote computer system 16 will have recorded essentially all the past glycemic history of each patient 13 so that the recommendation for an Insulin Dose is based upon the past history for that particular patient 13. For example, if the patient 13 at some past occasion had essentially the same conditions of blood glucose, food to be eaten, exercise, etc. as is now sent to the remote computer system 16 and on that prior occasion the remote computer system had sent a recommendation of 15 units of insulin to be delivered and that resulted in too low a subsequent reading of blood glucose, then at this time, the remote computer system would suggest an appropriately lower dose of insulin (for example 13 units) to optimize that patient's blood glucose. This system of having a computer adjust the insulin dose for a specific patient 13 based upon his/her prior experience has been shown in clinical trials to dramatically improve glycemic control as compared to the patient 13 merely guessing as to how many units of insulin to deliver under different circumstances. Thus, the use of the GlytApp with the system shown in FIG. 9 will significantly improve glycemic control for those diabetic patients who would use the concepts described herein. It has been clearly shown that improved glycemic control will decrease the possibility that the patient will suffer from heart disease, loss of a limb, loss of eyesight or any of the other problems typically associated with uncontrolled diabetes.

An important aspect of the glycemic control system 10 shown in FIG. 9 is that which occurs when the patient 13 is experiencing hypoglycemia or hyperglycemia. If either of those events occurs, then the remote computer system 16 will send an Out-of Range BG Alert to a company monitor 17 as shown in FIG. 9. Also, all readings of the patient's blood glucose indicated in FIG. 9 as the BG Reading can be sent to the company that has provided the GlytApp for that patient 13. Such data could also be sent directly to the physician 11 or it could be sent to the physician 11 through the company monitor 17. The physician 11 could directly contact the patient 13, or it could be arranged that the company monitor 17 informs the patient 13 of the Out-of-Range BG Reading and that monitor could also provide (as seen in FIG. 9) some Conversation-Instructions to guide that diabetic patient. The physician 11 could select either to contact the patient 13 directly or have any instructions to the patient 13 be provided by the company monitor 17. It is also understood that this system to "inform the patient's physician" could take place without any company monitor 17 being involved but rather would appear on the patient's smart phone.

By the use of the glycemic control system 10 shown in FIG. 9 it is possible to dramatically improve the glycemic control for any and all patients who would use a smart phone GlytApp as described herein.

Figure 10:
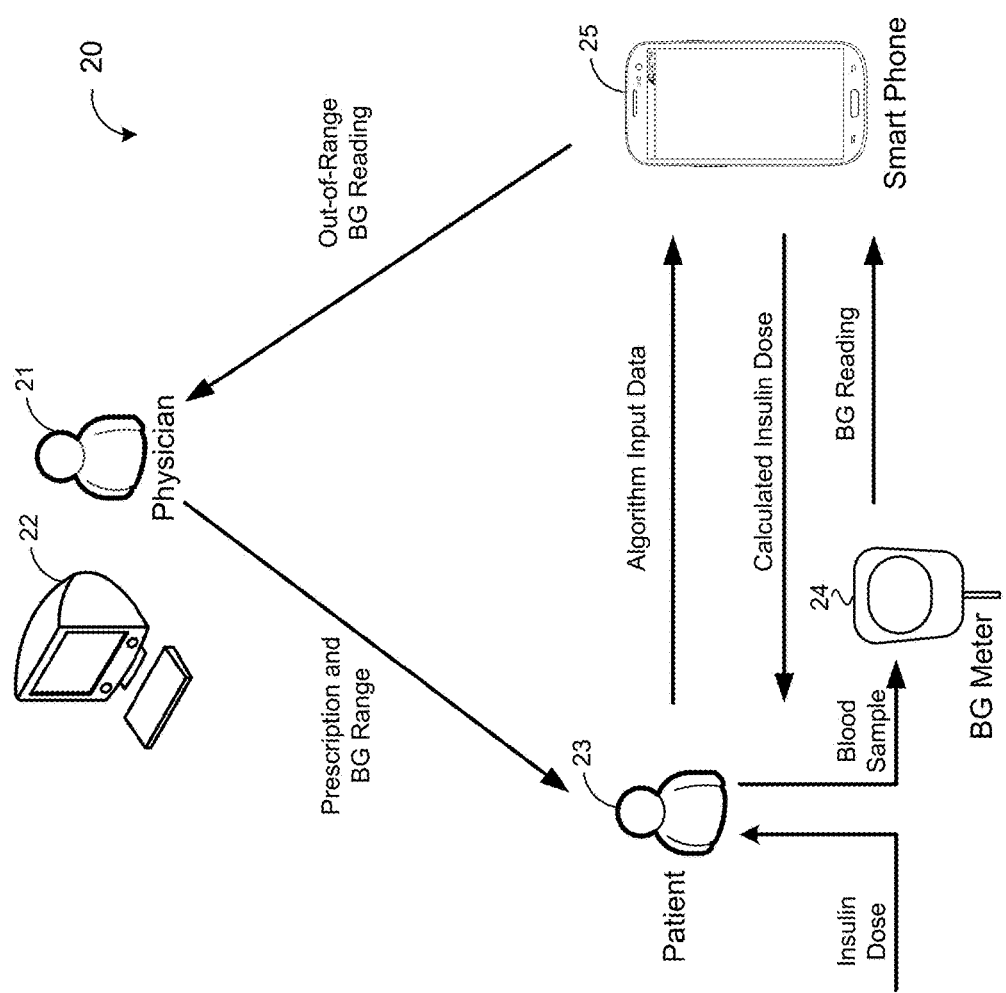
FIG. 10 is a system diagram for a novel system to improve glycemic control for a diabetic patient by using that patient's smart phone that has been programmed to make optimum suggestions as to the number of units of insulin to be delivered after the patient's level of blood glucose and other factors have been placed as inputs into that patient's smart phone.

FIG. 10 is a simplified system that uses a smart phone glycemic control system 20 to better control a patient's blood glucose without the use of a remote computer system. The glycemic control system 20 has the physician 21 use his computer 22 to provide for the patient 23 a Prescription and BG Range limits in a manner similar to that described for FIG. 9. For the system 20, all the calculations are accomplished within the smart phone 25 as operated by the patient 23. As with the system 10 of FIG. 9, the patient's blood glucose meter 24 is used to provide a Blood Sample that the blood glucose meter 24 uses to measure the blood glucose of the patient 23. When the patient 23 inputs all the Algorithm Input Data (as described above for FIG. 9) into the smart phone 25, the smart phone 25 does all the computation similar to the remote computer system 16 of FIG. 9, to provide the Calculated Insulin Dose as shown in FIG. 10. The patient 23 then injects the Calculated Insulin Dose as also shown in FIG. 10. As with the system of FIG. 9, if there is an Out-of-Range BG Reading, that information is sent to the physician 21 directly from the smart phone 25. The advantage of the system of FIG. 10 is that all the calculations are done within the smart phone 25 so that communication with a remote computer system is not needed. This system would be particularly valuable for patients who live or frequently travel to a region in the world where access to the Internet is limited or not available. The disadvantage of the system 20 is that a large remote computer system has much better computing power as compared to that which is typically available from a smart phone 25. It should be understood that the computer system in the smart phone 25 would have to provide the recommendation as to how many unit of insulin to inject based upon a large variety of input data as was described for the remote computer system 16 of FIG. 9.

Figure 11B:
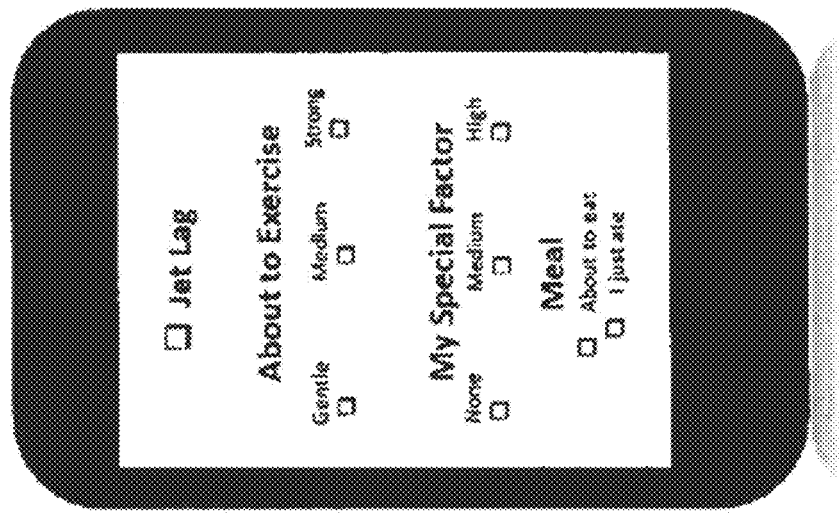
FIG. 11B is an extension of FIG. 11A that can be reached by scrolling down the smart phone screen.
Figure 11A:
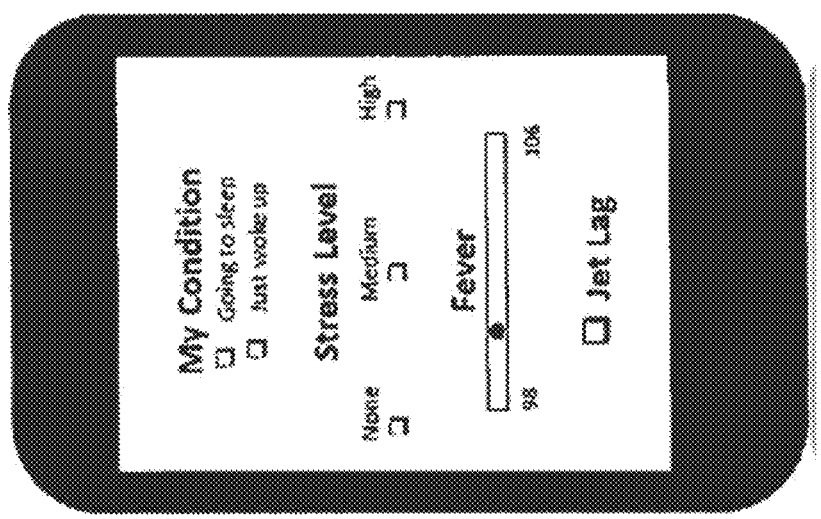
FIG. 11A shows the extended list of options that the patient may choose from to indicate conditions from his or her present situation that may factor into the dose of insulin needed.

FIG. 11A shows a list of options that the patient may choose from to indicate conditions about his or her present situation that may factor into the dose of insulin needed. These conditions include but are not limited to whether the patient is going to sleep or has just awakened, the current stress level of the patient, whether the patient has a fever and if so the severity of that fever, whether or not the patient is experiencing jet-lag, whether the patient is about to exercise and if so the severity of that exercise, whether the patient has just eaten or is about to eat, and any other special factors that pertain to the patient's current condition and the severity of those factors. Other factors not shown (such as having a menstrual period) may also be listed. If the patient does not give indication for any one of the options, it is taken to mean that that particular option is not currently a factor in the patient's condition. FIG. 11B is an extension of FIG. 11A that can be reached by scrolling down the smart phone screen.

Figure 12B:
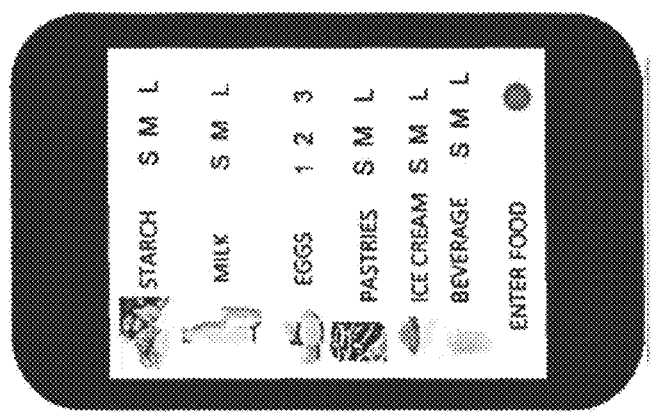
FIG. 12B is an extension of FIG. 12A that can be reached by scrolling down the smart phone screen.
Figure 12A:
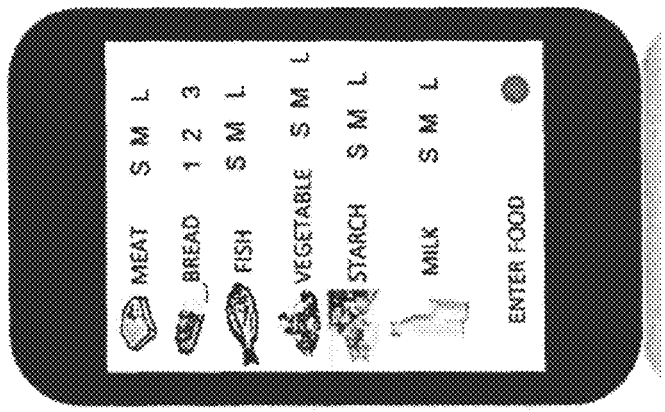
FIG. 12A shows a subset of all the foods that the patient has placed into his smart phone based upon what that specific patient would typically eat as selected from an extensive list of foods and including what the patient would deem to be either small, medium or large portions of that food.

FIG. 12A illustrates the type and quantity of foods that the patient has selected from an extensive list of such foods that that patient would regularly eat. From that subset on that patient's smart phone, the patient could communicate with a remote computer system or with his own smart phone to indicate the type and quantity of food that the patient is about to eat or has just eaten. The computer system in either the remote computer system 16 of FIG. 9 or the smart phone 25 of FIG. 10 would have in its memory the number of grams of carbohydrate for each of such foods. The quantity of food could be judged as to a small (S), medium (M) or large (L) portion as shown in FIGS. 12A and 12B. Also, any food that comes as pieces (such as slices of bread) could be indicated as to a number of pieces such as the numbers 1, 2 and 3 as shown for slices of bread in FIGS. 12A and 12B.

The lower portion of FIG. 13 displays on the patient's smart phone the expected range of insulin for that the patient based upon prior occasions when there were similar input parameters into either the remote computer system or the patient's smart phone. If the dose as suggested in FIG. 13 does not come within range of what is shown in the lower portion of FIG. 13, then the patient might request a rerun from the remote computer system or from his smart phone to make sure that the new reading is reasonable. FIG. 13 illustrates a typical LCD display that would be seen on the patient's smart phone that indicates to the patient that he is identified by name (John Smith) and either smart phone 15 or 25 is telling the patient how much insulin to inject depending on the input parameters that the patient put into the GlytApp. It is important that each patient knows that the information is personal for that specific patient. By having the patient's name displayed with the number of units of insulin to deliver, the patient immediately knows that this information is specifically for himself or herself.

Although this disclosure has been described in connection with specific forms and embodiments thereof, it will be appreciated that various modifications other than those discussed above may be resorted to without departing from the spirit or scope of the disclosure as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the disclosure as defined in the appended claims.

Various other modifications, adaptations and alternative designs are of course possible in light of the teachings as presented herein. Therefore it should be understood that, while still remaining within the scope and meaning of the appended claims, this disclosure could be practiced in a manner other than that which is specifically described herein.

What is claimed is:

1. A method comprising:
   obtaining, by data processing hardware, a target blood glucose range defined by upper and lower blood glucose limits for a patient from memory hardware;
   receiving, at the data processing hardware, a current blood glucose measurement of the patient and current patient condition parameters during a pre-meal time from a user device controlled by the patient and in communication with the data processing hardware, the current patient condition parameters comprising a number of carbohydrates consumed by the patient and an exercise parameter for the patient, and the pre-meal time associated with a meal type corresponding to one of breakfast, lunch, or dinner, wherein the user device is configured to:
   receive, in a user interface executing on the user device, inputs from the patient for each patient condition parameter; and transmit the current patient condition parameters from the user device to the data processing hardware;

determining, by the data processing hardware, whether the current blood glucose measurement is less than a midpoint of the target blood glucose range for the patient;

when the current blood glucose measurement is less than the midpoint of the target blood glucose range for the patient:
- determining, by the data processing hardware, carbohydrate intake instructions for the patient including a predetermined number of carbohydrates for the patient to ingest based on the exercise parameter; and
- transmitting the carbohydrate intake instructions to the user device, the carbohydrate intake instructions when received by the user device, causing the user interface executing on the user device to display the predetermined amount of carbohydrates for the patient to ingest;

determining, by the data processing hardware, a recommended meal bolus based on the number of carbohydrates consumed by the patient for the associated meal type;

obtaining, by the data processing hardware, previous patient condition parameters and a previous dosage of insulin administered by the patient for the associated meal type from the memory hardware, the previous patient condition parameters comprising a previous exercise parameter substantially equal to the exercise parameter associated with the current patient condition parameters;

obtaining, by the data processing hardware, a previous next scheduled blood glucose measurement from the memory hardware, the previous next scheduled blood glucose measurement resulting from the previous dosage of insulin administered by the patient;

determining whether the previous next scheduled blood glucose measurement is less than a hypoglycemia blood glucose limit for the patient;

when the previous next scheduled blood glucose measurement is less than the hypoglycemia blood glucose limit, determining, by the data processing hardware, a reduced insulin dosage value to prevent a next scheduled blood glucose measurement from falling below the hypoglycemia blood glucose limit;

subtracting, by the data processing hardware, the reduced insulin dosage value from the recommended meal bolus to determine a recommended dosage of insulin for the patient to administer; and transmitting the recommended dosage of insulin from the data processing hardware to the user device, the recommended dosage of insulin, when received by the user device, causing the user interface to display the recommended dosage of insulin.

2. The method of claim 1, wherein the exercise parameter comprises a duration and/or severity of an exercise planned by the patient or recently completed by the patient.

3. The method of claim 2, wherein determining the carbohydrate intake instructions including the predetermined number of carbohydrates comprises determining the predetermined number of carbohydrates for the patient to ingest based on the duration of the exercise.

4. The method of claim 2, wherein determining the carbohydrate intake instructions including the predetermined number of carbohydrates comprises determining the predetermined number of carbohydrates for the patient to ingest based on the severity of the exercise.

5. The method of claim 2, wherein determining the carbohydrate intake instructions including the predetermined number of carbohydrates comprises determining the predetermined number of carbohydrates for the patient to ingest based on the duration and the severity of the exercise.

6. The method of claim 1, wherein the target blood glucose range is inputted to the memory hardware by a medical professional computing device associated with an authorized medical professional.

7. The method of claim 1, further comprising, storing, by the data processing hardware, the recommended dosage of insulin and the current patient condition parameters in the memory hardware.

8. The method of claim 1, wherein determining the recommended meal bolus comprises:
- obtaining a carbohydrate-to-insulin ratio for the patient from the memory hardware, the carbohydrate-to-insulin ratio input to the memory hardware by a medical professional computing device associated with an authorized medical professional; and
- dividing the number of carbohydrates consumed by the patient by the carbohydrate-to-insulin ratio to determine the recommended meal bolus.

9. The method of claim 8, wherein the carbohydrate-to-insulin ratio is calculated as follows:

$$CIR = 450 \times TDD$$

wherein CIR is the carbohydrate-to-insulin ratio and TDD is a total prescribed daily dose of insulin for the patient based on a weight of the patient.

10. The method of claim 1, further comprising:
- obtaining, by the data processing hardware, an insulin sensitivity factor for the patient from the memory hardware, the insulin sensitivity factor inputted to the memory hardware by a medical professional computing device associated with an authorized medical professional;
- determining, by the data processing hardware, whether the current blood glucose measurement exceeds the midpoint of the target blood glucose range for the patient; and
- when the current blood glucose measurement exceeds the midpoint of the target blood glucose range for the patient:
  - determining, by the data processing hardware, a correction dose based on a function of the current blood glucose measurement, the mid-point of the target blood glucose range and the insulin sensitivity factor; and
  - transmitting the correction dose from the data processing hardware to the user device, the correction dose, when received by the user device, causing the user interface executing on the user device to display the correction dose.

11. The method of claim 1, wherein the user device is configured to:
- receive the current blood glucose measurement from a blood glucose meter in communication with the user device; and
- transmit the current blood glucose measurement of the patient to the data processing hardware.

12. The method of claim 1, wherein the user device is configured to:
- receive, in the user interface, a blood glucose input from the patient indicating the current blood glucose measurement; and transmit the current blood glucose measurement of the patient to the data processing hardware.

13. A system comprising:
a user device controlled by a patient and having a screen, the user device configured to:
   display the user interface on the screen; and
   receive, in the user interface displayed on the screen, inputs from the patient for patient condition parameters during a pre-meal time, the patient condition parameters comprising a number of carbohydrates consumed by the patient and an exercise parameter for the patient, and the pre-meal time associated with a meal type corresponding to one of breakfast, lunch, or dinner; and
data processing hardware in communication with the user device, the data processing hardware configured to perform operations comprising:
   obtaining a target blood glucose range defined by upper and lower blood glucose limits for the patient from memory hardware in communication with the data processing hardware;
   receiving a current blood glucose measurement of the patient during the pre-meal time from the user device;
   receiving the patient condition parameters input to the user interface during the pre-meal time from the user device;
   determining whether the blood glucose measurement is less than a midpoint of the target blood glucose range for the patient; and
   when the current blood glucose measurement is less than the midpoint of the target blood glucose range for the patient:
      determining carbohydrate intake instructions for the patient including a predetermined number of carbohydrates for the patient to ingest based on the exercise parameter; and
      transmitting the carbohydrate intake instructions to the user device, the carbohydrate intake instructions when received by the user device, causing the user interface executing on the user device to display the predetermined amount of carbohydrates for the patient to ingest;
   determining a recommended meal bolus based on the number of carbohydrates consumed by the patient for the associated meal type;
   obtaining previous patient condition parameters and a previous dosage of insulin administered by the patient for the associated meal type from the memory hardware, the previous patient condition parameters comprising a previous exercise parameter substantially equal to the exercise parameter associated with the current patient condition parameters;
   obtaining a previous next scheduled blood glucose measurement from the memory hardware, the previous next scheduled blood glucose measurement resulting from the previous dosage of insulin administered by the patient;
   determining whether the previous next scheduled blood glucose measurement is less than a hypoglycemia blood glucose limit for the patient;
   when the previous next scheduled blood glucose measurement is less than the hypoglycemia blood glucose limit, determining a reduced insulin dosage value to prevent a next scheduled blood glucose measurement from falling below the hypoglycemia blood glucose limit;
   subtracting the reduced insulin dosage value from the recommended meal bolus to determine a recommended dosage of insulin for the patient to administer; and
   transmitting the recommended dosage of insulin from the data processing hardware to the user device, the recommended dosage of insulin, when received by the user device, causing the user interface to display the recommended dosage of insulin.

14. The system of claim 13, wherein the exercise parameter comprises a duration and/or severity of an exercise planned by the patient or recently completed by the patient.

15. The system of claim 14, wherein determining the carbohydrate intake instructions including the predetermined number of carbohydrates comprises determining the predetermined number of carbohydrates for the patient to ingest based on the duration of the exercise.

16. The system of claim 14, wherein determining the carbohydrate intake instructions including the predetermined number of carbohydrates comprises determining the predetermined number of carbohydrates for the patient to ingest based on the severity of the exercise.

17. The system of claim 14, wherein determining the carbohydrate intake instructions including the predetermined number of carbohydrates comprises determining the predetermined number of carbohydrates for the patient to ingest based on the duration and the severity of the exercise.

18. The system of claim 13, further comprising a medical professional computing device associated with an authorized medical professional, the medical professional computing device configured to input the target blood glucose range to the memory hardware.

19. The system of claim 13, wherein the operations further comprise storing the recommended dosage of insulin and the current patient condition parameters in the memory hardware.

20. The system of claim 13, wherein determining the recommended meal bolus comprises:
   obtaining a carbohydrate-to-insulin ratio for the patient from the memory hardware, the carbohydrate-to-insulin ratio input to the memory hardware by a medical professional computing device associated with an authorized medical professional; and
   dividing the number of carbohydrates consumed by the patient by the carbohydrate-to-insulin ratio to determine the recommended meal bolus.

21. The system of claim 20, wherein the carbohydrate-to-insulin ratio is calculated as follows:

$$CIR = 450 \times TDD$$

wherein CIR is the carbohydrate-to-insulin ratio and TDD is a total prescribed daily dose of insulin for the patient based on a weight of the patient.

22. The system of claim 13, wherein the operations further comprise:
   obtaining an insulin sensitivity factor for the patient from the memory hardware, the insulin sensitivity factor inputted to the memory hardware by a medical professional computing device associated with an authorized medical professional;
   determining whether the current blood glucose measurement exceeds the midpoint of the target blood glucose range for the patient; and
   when the current blood glucose measurement exceeds the midpoint of the target blood glucose range for the patient:

determining a correction dose based on a function of the current blood glucose measurement, the midpoint of the target blood glucose range and the insulin sensitivity factor; and transmitting the correction dose from the data processing hardware to the user device, the correction dose, when received by the user device, causing the user interface executing on the user device to display the correction dose.

23. The system of claim 13, further comprising a blood glucose meter in communication with the user device and configured to measure blood glucose measurements of the patient, wherein the user device is configured to:

receive the current blood glucose measurement from the blood glucose meter; and transmit the current blood glucose measurement of the patient to the data processing hardware.

24. The system of claim 13, wherein the user device is configured to:

receive, in the user interface, a blood glucose input from the patient indicating the current blood glucose measurement; and transmit the current blood glucose measurement of the patient to the data processing hardware.

* * * * *